US009585853B2

(12) United States Patent
Darteil et al.

(10) Patent No.: US 9,585,853 B2
(45) Date of Patent: *Mar. 7, 2017

(54) USE OF 1,3-DIPHENYLPROP-2-EN-1-ONE DERIVATIVES FOR TREATING LIVER DISORDERS

(71) Applicant: GENFIT, Loos (FR)

(72) Inventors: Raphael Darteil, Lille (FR); Rémy Hanf, Lille (FR); Dean Hum, Bondues (FR); Ingrid Dufour, Wattignies (FR)

(73) Assignee: GENFIT, Loos (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/933,335

(22) Filed: Nov. 5, 2015

(65) Prior Publication Data
US 2016/0051501 A1 Feb. 25, 2016

Related U.S. Application Data

(63) Continuation of application No. 14/523,191, filed on Oct. 24, 2014, now Pat. No. 9,221,751, which is a continuation-in-part of application No. 14/288,482, filed on May 28, 2014, now Pat. No. 8,895,619, which is a continuation of application No. 13/511,170, filed as application No. PCT/EP2010/068346 on Nov. 26, 2010, now Pat. No. 8,772,342.

(30) Foreign Application Priority Data

Nov. 26, 2009 (EP) ..................... 09306146

(51) Int. Cl.
| | | |
|---|---|---|
| A61K 31/192 | (2006.01) |
| C07C 321/26 | (2006.01) |
| A61K 45/06 | (2006.01) |
| A61K 38/28 | (2006.01) |
| A61K 31/155 | (2006.01) |
| A61K 31/216 | (2006.01) |
| A61K 31/222 | (2006.01) |
| A61K 31/381 | (2006.01) |
| A61K 31/426 | (2006.01) |

(52) U.S. Cl.
CPC .......... *A61K 31/192* (2013.01); *A61K 31/155* (2013.01); *A61K 31/216* (2013.01); *A61K 31/222* (2013.01); *A61K 31/381* (2013.01); *A61K 31/426* (2013.01); *A61K 38/28* (2013.01); *A61K 45/06* (2013.01); *C07C 321/26* (2013.01)

(58) Field of Classification Search
CPC .............................. C07C 321/26; A61K 31/192
See application file for complete search history.

(56) References Cited

U.S. PATENT DOCUMENTS

| 5,691,373 | A | 11/1997 | Berryman et al. |
| 7,566,737 | B2 * | 7/2009 | Delhomel et al. ............. 514/432 |
| 8,258,182 | B2 * | 9/2012 | Delhomel et al. ............. 514/543 |
| 8,772,342 | B2 | 7/2014 | Darteil et al. |
| 8,895,619 | B2 | 11/2014 | Darteil et al. |
| 2005/0176808 | A1 | 8/2005 | Najib |
| 2007/0032543 | A1 | 2/2007 | Delhomel |
| 2010/0029757 | A1 | 2/2010 | Hellerbrand |
| 2010/0286276 | A1 | 11/2010 | Delhomel |
| 2012/0252725 | A1 | 10/2012 | Darteil et al. |
| 2014/0309165 | A1 | 10/2014 | Darteil et al. |
| 2015/0051145 | A1 | 2/2015 | Darteil et al. |

FOREIGN PATENT DOCUMENTS

| WO | WO 01/98291 | 12/2001 |
| WO | WO 2004/005233 | 1/2004 |
| WO | WO 2007/147879 | 12/2007 |
| WO | WO 2008/077618 | 7/2008 |

OTHER PUBLICATIONS

Tanaka et al, International Journal of Cancer, Hepatitis C virus core protein induces spontaneous and persistent activation of peroxisome proliferator-activated receptor a in transgenic mice: Implications for HCV-associated hepatocarcinogenesis, 2007, 122, pp. 124-131.*
Peters et al, Journal of Molecular Medicine, Peroxisome Proliferator-activated Receptor-a and Liver Cancer: Where Do Stand?, 2005, 83, pp. 774-785.*
Tolman et al, Diabetes Care, Spectrum of Liver Disease in Type 2 Diabetes and Management of Patients With Diabetes and Liver Disease, 2007, 30(3), pp. 734-743.*
Drugs@FDA: FDA Approved Drug Products—Fenofibrate—http://www.accessdata.fda.gov (Dec. 5, 2015).
Hepatic stellate cell, Wikipedia (May 2015).
Fernandez-Miranda et al., "A pilot trial of fenofibrate for the treatment of non-alcoholic fatty liver disease" Digestive and Liver Disease 40 (2008) 200-205.
Belfort et al., "A Placebo-Controlled Trial of Pioglitazone in Subjects with Nonalcoholic Steatohepatitis" N Engl J Med 2006;355:2297-307.
Cariou et al., "Effects of the New Dual PPAR α/δ Agonist GFT505 on Lipid and Glucose Homeostasis in Abdominally Obese PatientsWith Combined Dyslipidemia or Impaired Glucose Metabolism" Diabetes Care (2011) 34: pp. 2008-2014.
Cariou et al., "Dual Peroxisome Proliferator-Activated Receptor α/δ Agonist GFT505 Improves Hepatic and Peripheral Insulin Sensitivity in Abdominally Obese Subjects" (2013) Diabetes Care Publish Ahead of Print, published online May 28, 2013 care.diabetesjournals.org, with Supplemental data document.

(Continued)

*Primary Examiner* — Paul A Zucker
(74) *Attorney, Agent, or Firm* — Nixon & Vanderhye P.C.

(57) ABSTRACT

The invention provides 1,3-diphenylprop-2-en-1-one derivatives and pharmaceutical compositions comprising the same for treating liver disorders, in particular those requiring the reduction of plasma level of biochemical markers such as aminotransferases. The 1,3-diphenylprop-2-en-1-one derivatives of General Formula (I) have hepatoprotective properties and can be used in methods for treating liver disorders involving the pathological disruption, inflammation, degeneration, and/or proliferation of liver cells, such as liver fibrosis or fatty liver disease.

15 Claims, 4 Drawing Sheets

(56) References Cited

OTHER PUBLICATIONS

Chamberlain et al., "Protective Effects of the Carotenoid Zeaxanthin in Experimental Nonalcoholic Steatohepatitis" Dig Dis Sci (2009) 54: pp. 1460-1464.
Ip et al., "Administration of the Potent PPAR Agonist, Wy-14,643, Reverses Nutritional Fibrosis and Steatohepatitis in Mice" Hepatology (2004) 39: pp. 1286-1296.
Kudo et al., "Telmisartan attenuates progression of steatohepatitis in mice: role of hepaticmacrophage infiltration and effects on adipose tissue" Liver International (2009): pp. 1478-3223.
Miyahara et al., "PPAR and Hepatic Stellate Cell Activation" J. Biol. Chem. (2000) Published on Aug. 31, 2000 as Manuscript M006577200.
Nagasawa et al., "Effects of bezafibrate, PPAR pan-agonist, and GW501516, PPARδ agonist, on development of steatohepatitis in mice fed a methionine- and choline-deficient diet" European Journal of Pharmacology (2006) 536: pp. 182-191.
Nakano et al., "Bezafibrate prevents hepatic stellate cell activation and fibrogenesis in a murine steatohepatitis model, and suppresses fibrogenic response induced by transforming growth factor-β1 in a cultured stellate cell line" Hepatology Research (2008) 38: pp. 1026-1039.
Nan et al., "Antioxidants vitamin E and 1-aminobenzotriazole prevent experimental nonalcoholic steatohepatitis in mice" Scandinavian Journal of Gastroenterology (2009) 44: pp. 112-1131.
Nelson et al., "A Pilot Study Using Simvastatin in the Treatment of Nonalcoholic Steatohepatitis A Randomized Placebo-controlled Trial" J Clin Gastroenterol (2009) 43: pp. 990-994.
Neuschwander-Tetri et al., "Improved Nonalcoholic Steatohepatitis After 48 Weeks of Treatment With the PPAR-Ligand Rosiglitazone" Hepatology (2003) 38: pp. 1008-1017.
Shiri-Sverdlov et al., "Early diet-induced non-alcoholic steatohepatitis in APOE2 knock-in mice and its prevention by fibrates" Journal of Hepatology (2006) 44: pp. 732-741.
Staels et al., "Hepatoprotective Effects of the Dual Peroxisome Proliferator-Activated Receptor Alpha=Delta Agonist, GFT505, in Rodent Models of Nonalcoholic Fatty Liver Disease/Nonalcoholic Steatohepatitis" Hepatology (2013) 58: pp. 1941-1952 (with supplemental Figures 1 and 2 and data).
Tahan et al., "Rosiglitazone Attenuates Liver Inflammation in a Rat Model of Nonalcoholic Steatohepatitis" Dig Dis Sci (2007) 52: pp. 3465-3472.
Witek et al., "Pan-Caspase Inhibitor VX-166 Reduces Fibrosis in an Animal Model of Nonalcoholic Steatohepatitis" Hepatology (2009) 50: pp. 1421-1430.
Xu et al., "Activation of peroxisome proliferator-activated receptor—contributes to the inhibitory effects of curcumin on rat hepatic stellate cell growth" Am J Physiol Gastrointest Liver Physiol (2003) 285: pp. G20-G30.
International Search Report for PCT/EP2010/068346 mailed Mar. 2, 2011.
Written Opinion for PCT/EP2010/068346 mailed Mar. 2, 2011.
International Preliminary Report on Patentability for PCT/EP201/068346, mailed Mar. 6, 2012.
Tanaka et al, "Hepatitis C virus core protein induces spontaneous and persistent activation of peroxisome proliferator-activated recepor a in transgenic mice: Implications for HCV-associated hepatocarcinogenesis" International Journal of Cancer, 2007, 122, pp. 124-131.
Peters et al, "Peroxisome Proliferator-activated Receptor-a and Liver Cancer: Where do Stand", Journal of Molecular Medicine, 2005, 83, pp. 774-785.
Kallwitz et al, "Role of Peroxisome Proliferator-activated Receptors in the Pathogenesis and Treatment of Nanalcoholic Fatty Liver Disease", World Journal of Gastroenterology, 2008, 14(1), pp. 22-28.
Declaration of Dr. Remy Hanf executed Apr. 15, 2014 and filed in U.S. Appl. No. 13/511,170.
Washington Manual of Medical Therapeutics, Green et al (Editors), 31st Edition.; 2004; Lippincott Williams & Wilkins, Liver Diseases, pp. 378-397.

\* cited by examiner

A)

B)

C)

A)

C)

B)

D)

SEQUENCE LISTING

<160> NUMBER OF SEQ ID NOS: 16

<210> SEQ ID NO 1
<211> LENGTH: 25
<212> TYPE: DNA
<213> ORGANISM: artificial
<220> FEATURE:
<223> OTHER INFORMATION: 36B4 reverse primer

<400> SEQUENCE: 1
gggaaggtgt aatccgtctc cacag          25

<210> SEQ ID NO 2
<211> LENGTH: 25
<212> TYPE: DNA
<213> ORGANISM: artificial
<220> FEATURE:
<223> OTHER INFORMATION: 36B4 forward primer

<400> SEQUENCE: 2
catgctcaac atctcccect tctcc          25

<210> SEQ ID NO 3
<211> LENGTH: 20
<212> TYPE: DNA
<213> ORGANISM: artificial
<220> FEATURE:
<223> OTHER INFORMATION: TNFa reverse primer

<400> SEQUENCE: 3
aggtacaacc catcggctgg          20

<210> SEQ ID NO 4
<211> LENGTH: 22
<212> TYPE: DNA
<213> ORGANISM: artificial
<220> FEATURE:
<223> OTHER INFORMATION: TNFa forward primer

<400> SEQUENCE: 4
cgtcgtagca aaccaccaag tg          22

<210> SEQ ID NO 5
<211> LENGTH: 20
<212> TYPE: DNA
<213> ORGANISM: artificial
<220> FEATURE:
<223> OTHER INFORMATION: TGFb reverse primer

<400> SEQUENCE: 5
tggttgtaga gggcaaggac          20

<210> SEQ ID NO 6
<211> LENGTH: 20
<212> TYPE: DNA
<213> ORGANISM: artificial
<220> FEATURE:
<223> OTHER INFORMATION: TGFb forward primer

<400> SEQUENCE: 6
ttgcttcagc tccacagaga          20

<210> SEQ ID NO 7
<211> LENGTH: 20
<212> TYPE: DNA
<213> ORGANISM: artificial
<220> FEATURE:
<223> OTHER INFORMATION: CCL5 reverse primer

<400> SEQUENCE: 7
cacacttggc ggttccttcg          20

<210> SEQ ID NO 8
<211> LENGTH: 22
<212> TYPE: DNA

```
<213> ORGANISM: artificial
<220> FEATURE:
<223> OTHER INFORMATION: CCL5 forward primer

<400> SEQUENCE: 8
ccctcaccat catcctcact gc                                              22

<210> SEQ ID NO 9
<211> LENGTH: 19
<212> TYPE: DNA
<213> ORGANISM: artificial
<220> FEATURE:
<223> OTHER INFORMATION: Col1a1 reverse primer

<400> SEQUENCE: 9
gccaggagaa ccagcagag                                                  19

<210> SEQ ID NO 10
<211> LENGTH: 20
<212> TYPE: DNA
<213> ORGANISM: artificial
<220> FEATURE:
<223> OTHER INFORMATION: Col1a1 forward primer

<400> SEQUENCE: 10
aggcgaacaa ggtgacagag                                                 20

<210> SEQ ID NO 11
<211> LENGTH: 20
<212> TYPE: DNA
<213> ORGANISM: artificial
<220> FEATURE:
<223> OTHER INFORMATION: aSMA forward primer

<400> SEQUENCE: 11
actgccttgg tgtgtgacaa                                                 20

<210> SEQ ID NO 12
<211> LENGTH: 20
<212> TYPE: DNA
<213> ORGANISM: artificial
<220> FEATURE:
<223> OTHER INFORMATION: aSMA reverse primer

<400> SEQUENCE: 12
tggtgatgat gccatgttct                                                 20

<210> SEQ ID NO 13
<211> LENGTH: 20
<212> TYPE: DNA
<213> ORGANISM: artificial
<220> FEATURE:
<223> OTHER INFORMATION: Col1a1 forward primer

<400> SEQUENCE: 13
aatggtgctc ctggtattgc                                                 20

<210> SEQ ID NO 14
<211> LENGTH: 20
<212> TYPE: DNA
<213> ORGANISM: artificial
<220> FEATURE:
<223> OTHER INFORMATION: Col1a1 reverse primer

<400> SEQUENCE: 14
accaggttca ccgctgttac                                                 20
```

```
<210> SEQ ID NO 15
<211> LENGTH: 20
<212> TYPE: DNA
<213> ORGANISM: artificial
<220> FEATURE:
<223> OTHER INFORMATION: Col4a1 forward

<400> SEQUENCE: 15
gttggtctac cgggactcaa                                               20

<210> SEQ ID NO 16
<211> LENGTH: 20
<212> TYPE: DNA
<213> ORGANISM: artificial
<220> FEATURE:
<223> OTHER INFORMATION: Col4a1 reverse primer

<400> SEQUENCE: 16
gttcacctct gatcccctga                                               20
```

USE OF 1,3-DIPHENYLPROP-2-EN-1-ONE DERIVATIVES FOR TREATING LIVER DISORDERS

This application is a continuation of application Ser. No. 14/523,191 (published as US 2015-0051145 A1), filed Oct. 24, 2014 (issued as U.S. Pat. No. 9,221,751), which is a continuation-in-part of application Ser. No. 14/288,482 (issued as U.S. Pat. No. 8,895,619), filed May 28, 2014 (published as US 2014-0309165 A1), which is a continuation of application Ser. No. 13/511,170, filed May 22, 2012 (issued as U.S. Pat. No. 8,772,342), which is a U.S. National Phase of International Application No. PCT/EP2010/068346, filed 26 Nov. 2010, which designated the U.S. and claims priority to European Patent Application No. 09306146.3, filed 26 Nov. 2009, the entire contents of each of which are hereby incorporated by reference.

TECHNICAL FIELD

The invention relates to the use of compounds having hepatoprotective effects in the preparation of pharmaceutical compositions and in methods for treating liver disorders.

BACKGROUND

According to the Washington Manual of Medical Therapeutics (31$^{st}$ ed.; 2004; Lippincott Williams & Wilkins), liver disorders can be categorized in different groups of diseases, in particular viral diseases, drug- and alcohol-related liver diseases, immune-mediated liver diseases, metabolic liver diseases, miscellaneous diseases such as non-alcoholic fatty liver disease, and complications of hepatic insufficiency (such as fulminant hepatic failure or hepatocellular carcinoma) and of liver transplantation.

In particular, non-alcoholic fatty liver disease (NAFLD) is a common hepatic disorder with histological features of alcohol-induced fatty liver disease in individuals who consume little or no alcohol (Yeh M et al., 2007; Marchesini G et al., 2003). NAFLD is due to the abnormal retention of lipids within cells (commonly defined as steatosis), an event more frequent in liver since this organ is primarily responsible of lipid metabolism. NAFLD has a spectrum of histological forms including hepatic steatosis, and non-alcoholic steatohepatitis (NASH), which is characterized by liver inflammation, steatosis, necrosis and fibrosis due to the disruption of liver cells. Conditions associated with NAFLD are varied, and include type 2 diabetes, obesity, dyslipidemia, metabolic syndrome, treatment with hepatotoxic drugs, toxins, infectious agents, or other exogenous causes.

Although NAFLD typically follows a benign, non-progressive clinical course, NASH is a potentially serious condition; as many as 25% of patients may progress to advanced fibrosis, cirrhosis and experience complications of portal hypertension, liver failure and hepatocellular carcinoma, which makes an early and correct assessment mandatory (Yeh M et al, 2007).

Hepatic imaging systems are useful to evaluate also liver structure and presence of steatosis. However, liver biopsy remains the gold standard for evaluating liver fibrosis, but this method of analysis could not be done for every single study due to its invasiveness. Non invasive evaluation of liver biochemistry and metabolism is often used to define liver diseases, such as in NAFLD and NASH (Gressner A et al., 2009; Vuppalanchi R and Chalasani N, 2009). By using plasma, high level of enzymes such as Alanine aminotransferase (ALAT), Aspartate aminotransfersase (ASAT), Alkaline Phosphatase (AP), and/or Gamma Glutamyl Transpeptidase (GGT), as well as the presence of other proteins of liver origin (including haptoglobin, total bilirubin, alpha-2-microglobulin, Resistin, cleaved or intact cytokeratin-18) are commonly measured in addition to serum glucose and insulin resistance parameters. Since the level of ALAT activity is frequently increased in NASH patients (Angulo P et al, 2002), this criteria is considered as a surrogate marker for assessing liver injury. In fact, reliable non-invasive methods are not available to correctly diagnose NAFLD or NASH and even the histological features are not always sufficient to distinguish properly NAFLD or NASH from other conditions such as alcoholic liver disease (Yeh M et al., 2007, Vuppalanchi R and Chalasani N, 2009).

Means for an effective treatment for liver fibrotic diseases, and NAFLD and NASH in particular, are still insufficient. No treatment is established for patient with NASH, and several therapeutic options are tested in clinical trial (Vuppalanchi R and Chalasani N, 2009, Dowman J. K et al., 2009). These studies involve the use of many different families of chemical compounds (fibrates, thiazolidinediones, biguanides, statins, cannabinoids) and therapeutic targets (nuclear receptors, angiotensin receptors, cannabinoid receptors, HMG-CoA reductase). Recently, studies involving thiazolidinediones (Rosiglitazone and Pioglitazone) have shown that these drugs may improve liver condition but treatment with these drugs is not without undesired effects such as higher risks of congestive cardiac failure and osteoporosis, as well as weight gain with psychological effects on the patient (Dowman J. K et al., 2009; Shiri-Sverdlov R et al., 2006; Neuschwander-Tetri et al., 2003). Clinical trials involving the administration of cannabinoids have raised the concern of neuropsychiatric disruption (Vuppanchi R and Chalasani N, 2009). Other therapies currently ongoing are seeking to assess in NASH drugs as antioxidants but none of these treatments has yet showed convincing results (Nelson A et al., 2009).

The need for novel therapeutic options for the management of liver disorders, in particular those involving liver fibrosis and/or steatosis, is still clear and urgent.

SUMMARY OF INVENTION

A clinical study has surprisingly shown that the treatment of patients with a 1,3-diphenylprop-2-en-1-one derivative provides a statistically relevant reduction of liver-specific biochemical markers in the plasma, demonstrating the hepatoprotective properties of a family of compounds that is defined by means of a General Formula (I).

The present invention provides novel 1,3-diphenylprop-2-en-1-one derivatives of General Formula (I) (said derivatives being elsewhere also referred to as the "compounds") or pharmaceutical compositions comprising the same for use in a method for treating liver disorders, in particular those ones that lead to the increase of plasma level of biochemical markers such as aminotransferases. The 1,3-diphenylprop-2-en-1-one derivatives of General Formula (I) and pharmaceutical compositions comprising the same have hepatoprotective properties and can be used in methods for treating liver disorders involving the pathological disruption, inflammation, degeneration, and/or proliferation of liver cells, such as liver fibrosis, fatty liver disease and non-alcoholic steatohepatitis.

Further objects of the present invention, including specific general formulas of the compounds of interest, are provided in the Detailed Description.

DESCRIPTION OF THE FIGURES

Abbreviations Used in the Figures and in the Text

ALAT=alanine aminotransferase
CCL5=chemokine (C—C motif) ligand 5
Col1a1=collagen, type I, alpha 1
Cpd 1=compound 1 of WO2007/147879
Cpd 29=compound 29 of WO2004/005233
Ctrl=control or vehicle
Feno=Fenofibrate
HDL=High Density Lipoprotein
LDL=Low Density Lipoprotein
NAFLD=Non-alcoholic fatty liver disease
NASH=Non-alcoholic steatohepatitis
PPAR=Peroxisome Proliferator Activated Receptor
Rosi=Rosiglitazone
RT-PCR=Reverse Transcription Polymerase Chain Reaction
TGFβ=Transforming Growth Factor beta
TNFα=Tumor Necrosis Factor alpha

Exemplary compounds of the General Formula (I) are grouped according to the more specific definitions of General Formula (II) (Panel A), of General Formula (IV) (Panel B), and of General Formula (V) (Panel C).

Figure 2:
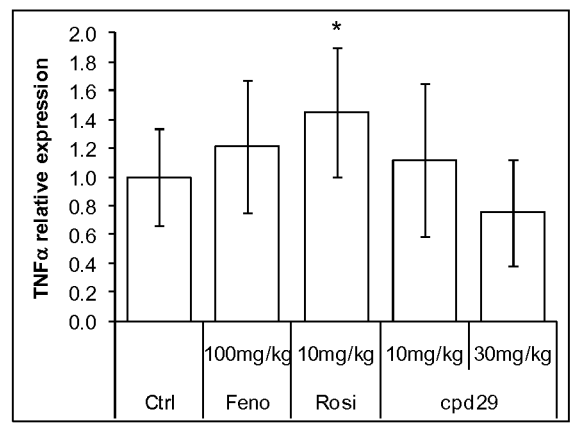
Figure 2:
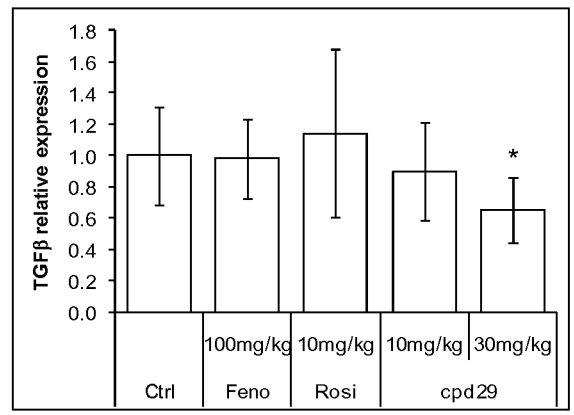
Figure 2:
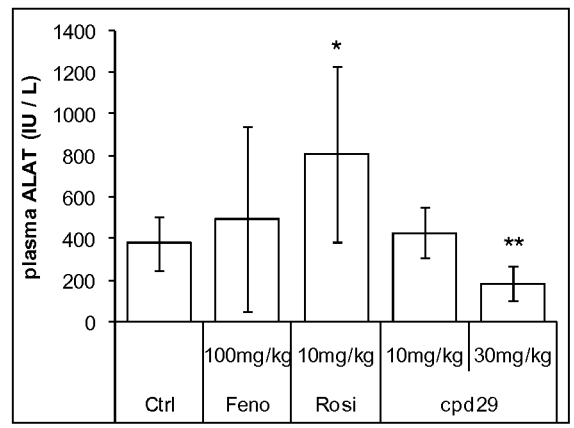

FIG. 2 In Vivo Evaluation, in the ob/ob Mice, of the Anti-Inflammatory Properties of Compounds of the General Formula (I)

The compounds of the General Formula (I) were tested in a murine model of type II diabetes, the ob/ob mice. Mice were daily orally treated with the Compound 29 of WO2004/005233 at two different doses (10 and 30 mg/kg/day) and with the prototypical PPARalpha- and PPARgamma-specific reference compounds (Fenofibrate at 100 mg/kg/day and Rosiglitazone at 10 mg/kg/day respectively). After 26 days of treatment, animals were sacrificed and plasma samples and livers were harvested. Hepatic expression of genes that are known to be implicated in the liver inflammation process was evaluated and plasmatic levels of ALAT were measured (Panels A-C). Statistical analysis was performed using unpaired T-test with three p values that defines statistical relevance (* means $p<0.05$;  means $p<0.01$; * means $p<0.001$).

Figure 3:
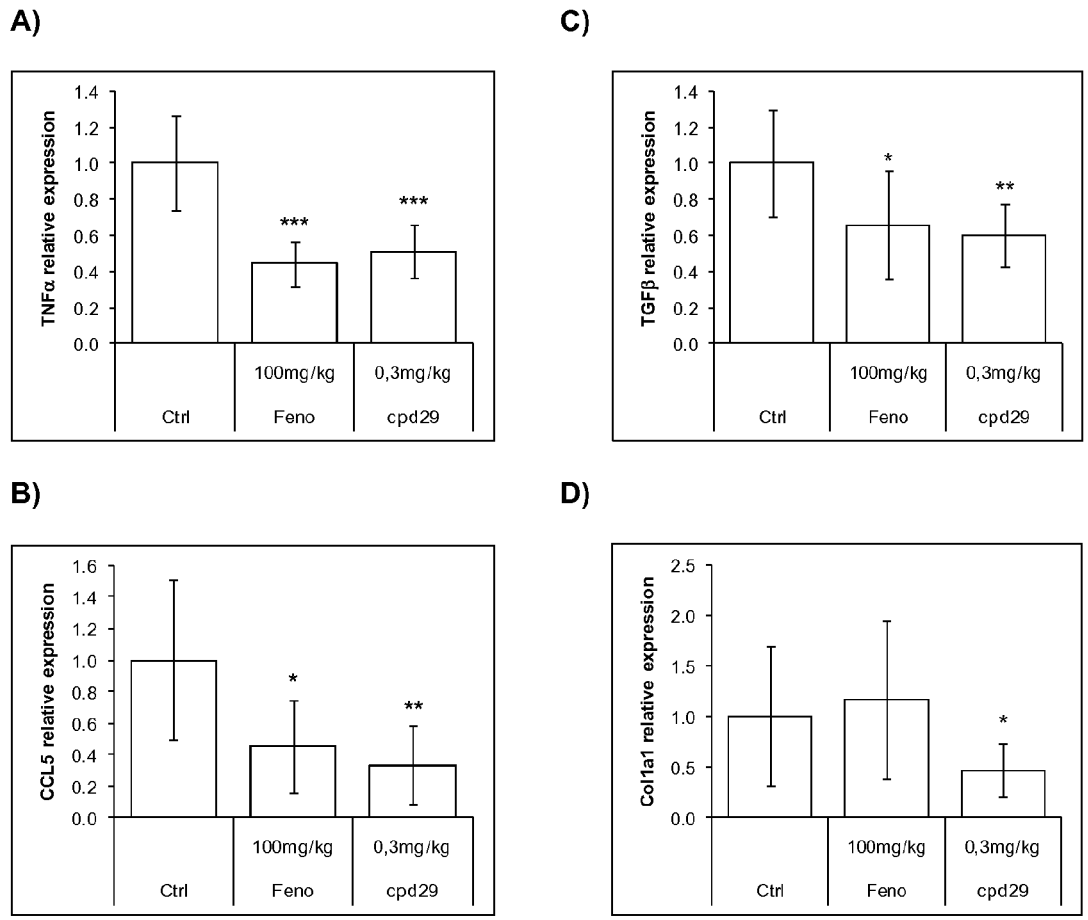

FIG. 3: In Vivo Evaluation, in the hApoE2 KI Mice, of the Anti-Inflammatory and Anti-Fibrotic Properties of Compounds of the General Formula (I)

Figure 1:
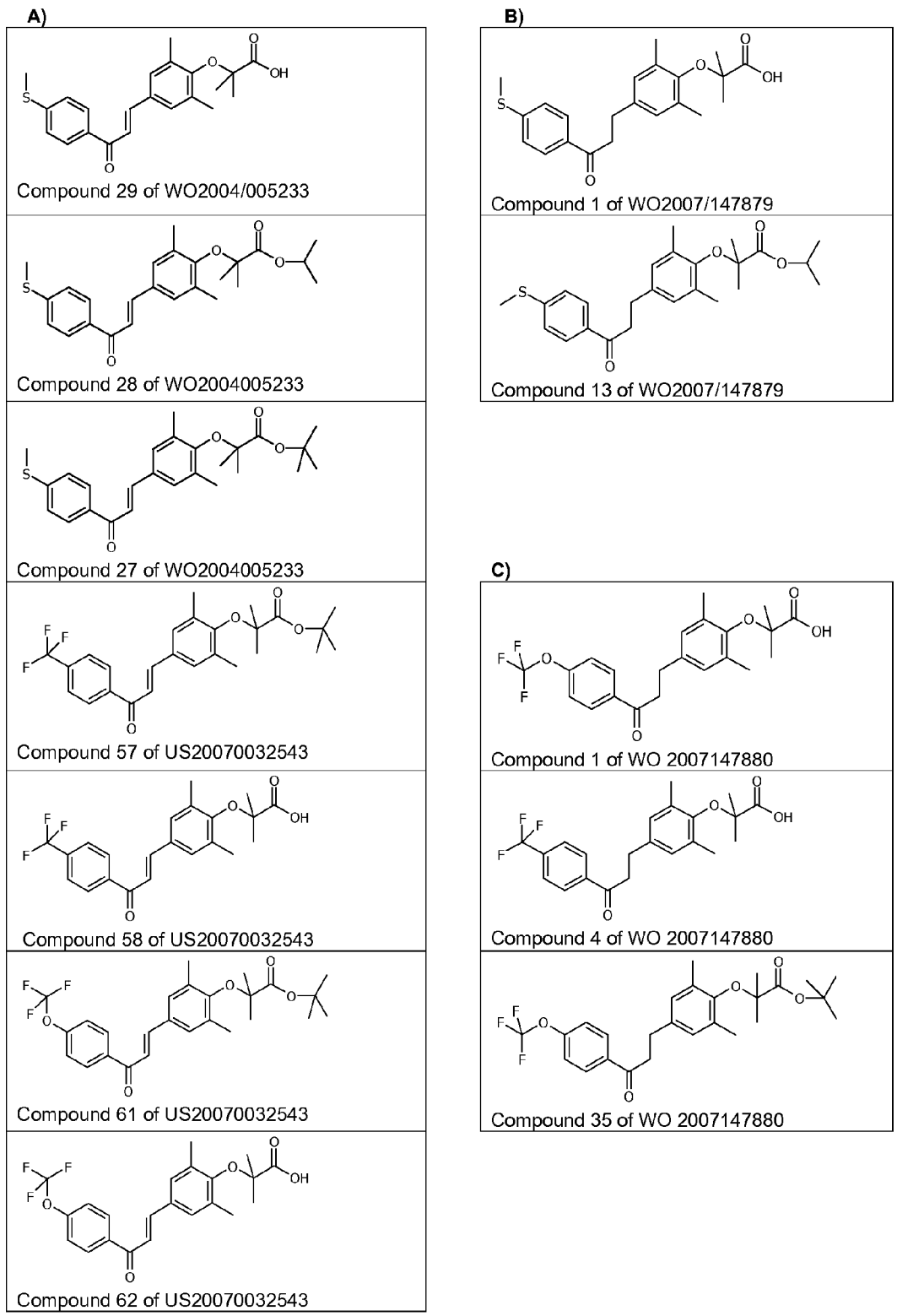
FIG. 1: Structure of Exemplary Compounds of General Formula (I)

The compounds of the General Formula (I) were tested in vivo in a high fat diet mice model. Dyslipidemic "humanized" ApoE knock-in mice (hApoE2 KI) were fed a Western diet and treated during 12 weeks. The compounds of interest, including the Compound 29 of WO2004/005233 at 0.3 mg/kg/day and the Fenofibrate at 100 mg/kg/day (used as a reference compound) were incorporated into the diet. At the end of the protocol, animals were sacrificed, livers were harvested and the hepatic expression of genes that are known to be implicated in the liver inflammation and the fibrosis processes were evaluated by quantitative RT-PCR (Panels A-D). Statistical analysis was performed as indicated for FIG. 1.

Figure 4:
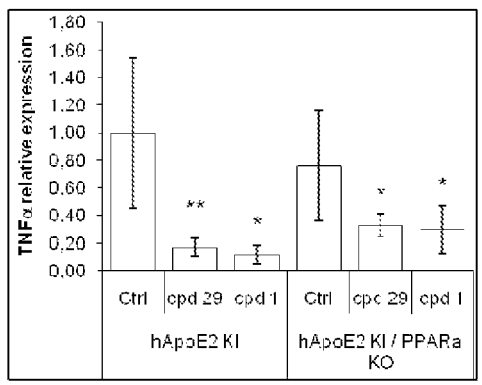
Figure 4:
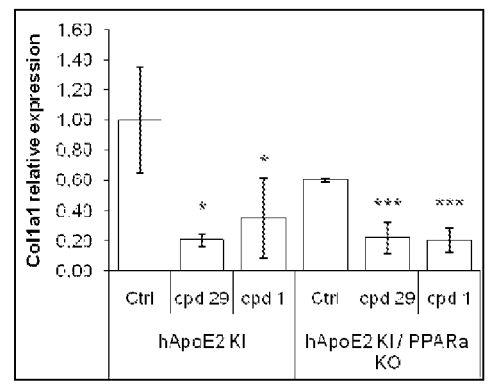
Figure 4:
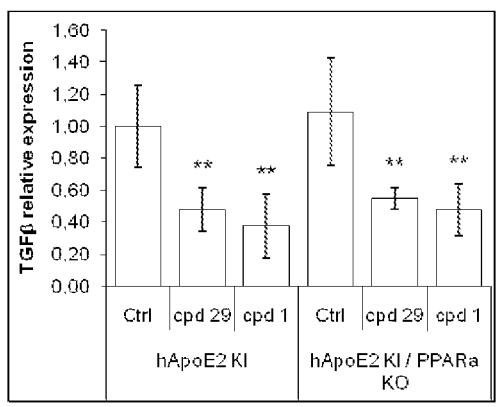
Figure 4:
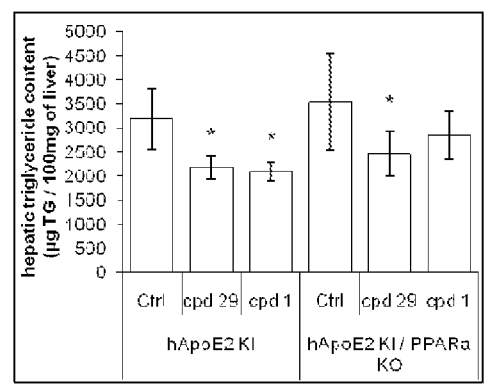

FIG. 4. In Vivo Evaluation, in the hApoE2 KI and in the hApoE2 KI/PPARalpha KO Mice, of the Anti-Inflammatory and Anti-Steatotic Properties of Compounds of the General Formula (I)

The compounds of the General Formula (I) were tested in vivo in a high fat diet mice model. Dyslipidemic "humanized" hApoE2 KI deficient for PPARalpha were fed a Western diet and treated during 6 weeks. The compounds of interest, including the Compound 29 of WO2004/005233 at 30 mg/kg/day and the Compound 1 of WO2007/147879 at 30 mg/kg/day were orally administered by gavage. At the end of the protocol, animals were sacrificed, livers were harvested and the hepatic expression of relevant genes implicated in the liver inflammation and the fibrosis processes were evaluated by quantitative RT-PCR. In parallel, liver triglycerides contents were evaluated (Panels A-D). Statistical analysis was performed as indicated for FIG. 1.

DETAILED DESCRIPTION OF THE INVENTION

The present invention provides novel therapeutic uses and methods of administration of 1,3-diphenylprop-2-en-1-one derivatives of General Formula (I) and pharmaceutical compositions comprising the same for treating liver disorders. Specific 1,3-diphenylprop-2-en-1-one derivatives that are substituted on both phenyl groups can be defined according to the Examples as being useful for treating liver disorders, since such compounds decrease in a surprising manner specific markers of liver inflammation as well as of the disruption, degeneration, and/or proliferation of liver cells in human subjects and animal models, and thus they can provide an hepatoprotective effect.

The compounds to be used and administered according to the invention and comprised in the compositions according to the invention have the following General Formula (I):

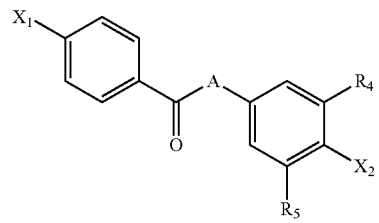

in which:
X1 represents a halogen, a R1, or G1-R1 group;
A represents a CH═CH or a CH2—CH2 group;
X2 represents a G2-R2 group;
G1 and G2, identical or different, represent an atom of oxygen or sulfur;
R1 represents a hydrogen atom, an unsubstituted alkyl group, an aryl group or an alkyl group that is substituted by one or more halogen atoms, an alkoxy or an alkylthio group, cycloalkyl groups, cycloalkylthio groups or heterocyclic groups;
R2 represents an alkyl group substituted by at least a —COOR3 group, wherein R3 represents a hydrogen atom, or an alkyl group that is substituted or not by one or more halogen atoms, cycloalkyl groups, or heterocyclic groups.
R4 and R5, identical or different, representing an alkyl group that is substituted or not by one or more halogen atoms, cycloalkyl groups, heterocyclic groups.

In a particular embodiment, compounds of General Formula (I) are substituted by at least an alkyloxy group or an alkylthio group in X1 and X2 positions. Moreover, the derivatives can be in the form of substituted 1,3-diphenylpropanones that are obtained by reduction of the corresponding 1,3-diphenylprop-2-en-1-one derivatives.

In a particular embodiment, X1 is a G1-R1 group, and more preferably G1 is a sulfur atom and R1 is a linear or branched alkyl group that is substituted or not by one or more halogen atoms, cycloalkyl groups, heterocyclic groups. Even more preferably, X1 is an alkylthio group that comprises an alkyl group that is linear or branched, having from one to seven carbon atoms that is substituted or not by one or more halogen atoms. In a preferred embodiment, X1 is a methylthio group.

In a particular embodiment, X2 is a G2-R2 group wherein G2 is a oxygen atom and R2 is an alkyl group substituted by a —COOR3 group, wherein R3 represents a hydrogen atom or an unsubstituted linear or branched alkyl group having from one to seven carbon atoms, and more preferably from one to four carbon atoms. In a preferred embodiment, both R4 and R5 represent methyl groups.

Furthermore, R4 and R5, identical or different, are preferably unsubstituted linear branched, alkyl groups having from one to seven carbon atoms, and more preferably from one to four carbon atoms.

In the context of the present invention, the term "alkyl" refers to a saturated hydrocarbon radical that is linear or branched, having preferably from one to twenty-four, and even more preferably from one to seven carbon atoms, such as methyl, ethyl, n-propyl, isopropyl, n-butyl, isobutyl, tertiobutyl, sec-butyl, pentyl, neopentyl, or n-hexyl.

The term "alkyloxy" refers to an alkyl group that is linked to the remainder of the compound by an oxygen atom.

The term "alkylthio" refers to an alkyl group that is linked to the remainder of the compound by a sulfur atom (thioether bond).

The term "cycloalkyl" designates an alkyl group that forms one cycle having preferably from three to fourteen carbon atoms, and more preferably three to eight carbon atoms, such as cyclopropyl, cyclobutyl, cyclopentyl, cyclohexyl, cycloheptyl, and cyclooctyl.

The term "cycloalkylthio" refers to a cycloalkyl group that is linked to the remainder of the compound by a sulfur atom (thioether bond).

The term "aryl" designates an aromatic group, substituted or not having preferably from six to fourteen carbon atoms such as phenyl, a-naphtyl, b-naphtyl, biphenyl, or anthracenyl.

The term "heterocyclic" refers to a heterocycloalkyl group or a heteroaryl group.

The term "heterocycloalkyl" group refers to a cycloalkyl as indicated above that further comprises one or several heteroatoms selected among nitrogen, oxygen or sulfur. They generally comprise from four to fourteen carbon atoms, such as morpholinyl, piperidinyl, tetrahydropyranyl, dithiolanyl.

The term "heteroaryl" refers to an aryl group as indicated above that further comprises one or several heteroatoms selected among nitrogen, oxygen or sulfur. They generally comprise from four to fourteen carbon atoms, such as furanyl, thiophenyl, pyridinyl, pyrimidinyl, quinoleinyl, isoquinoleinyl.

By halogen atom, an atom of bromine, chlorine, fluorine or iodine is understood.

Different families of 1,3-diphenylprop-2-en-1-one derivatives and 1,3-diphenylpropanones that are substituted on both phenyl groups can be found in the prior art (WO2003/037315, WO2001/046110, JP2006-303800, JP04-202129). However, none of these documents shows that specific hepatoprotective effects are associated to compounds as defined in General Formula (I).

The structure, synthesis, and some activities of compounds that are encompassed by General Formula (I) have been disclosed in a series of patent applications (WO2004/005243, WO2004/005233, WO2005/005369, US20070032543, WO2005/073184, WO2007/147879, and WO2007/147880) that do not disclose the use of such compounds in methods for treating liver disorders.

Specific 1,3-diphenylprop-2-en-1-one derivatives of General Formula (I) that can be used in the present invention and that can be comprised in compositions according to the invention can be selected from those disclosed in WO2004/005243 and WO2004/005233, and in particular:

1-[4-chlorophenyl]-3-[3,5-dimethyl-4-isopropyloxycarbonyldimethylmethyloxyphenyl]prop-2-en-1-one, described as compound 15;

1-[4-chlorophenyl]-3-[3,5-dimethyl-4-tertbutyloxycarbonyldimethylmethyloxyphenyl]prop-2-en-1-one, described as compound 16;

1-[4-chlorophenyl]-3-[3,5-dimethyl-4-carboxydimethylmethyloxyphenyl]prop-2-en-1-one as compound 17;

1-[4-methylthiophenyl]-3-[3,5-dimethyl-4-tertbutyloxycarbonyldimethylmethyloxyphenyl]prop-2-en-1-one, described as compound 27;

1-[4-methylthiophenyl]-3-[3,5-dimethyl-4-isopropyloxycarbonyldimethylmethyloxyphenyl]prop-2-en-1-one, described as compound 28;

1-[4-methylthiophenyl]-3-[3,5-dimethyl-4-carboxydimethylmethyloxyphenyl]prop-2-en-1-one, described as compound 29;

1-[4-hexyloxyphenyl]-3-[3,5-dimethyl-4-tertbutyloxycarbonyldimethylmethyloxyphenyl]prop-2-en-1-one, described as compound 32;

1-[4-hexyloxyphenyl]-3-[3,5-dimethyl-4-carboxydimethylmethyloxyphenyl]prop-2-en-1-one, described as compound 33;

1-[4-heptylphenyl]-3-[3,5-dimethyl-4-tertbutyloxycarbonyldimethylmethyloxyphenyl]prop-2-en-1-one, described as compound 38;

1-[4-heptylphenyl]-3-[3,5-dimethyl-4-carboxydimethylmethyloxyphenyl]prop-2-en-1-one, described as compound 39;

1-[4-bromophenyl]-3-[3,5-dimethyl-4-tertbutyloxycarbonyldimethylmethyloxyphenyl]prop-2-en-1-one, described as compound 40;

1-[4-bromophenyl]-3-[3,5-dimethyl-4-carboxydimethylmethyloxyphenyl]prop-2-en-1-one, described as compound 41.

In a further embodiment of the invention, the compounds as disclosed in WO2004/005243 and WO2004/005233 (herein referred to as compounds of General Formula (II)) that can be used and administered and that can be comprised in compositions according to the invention have the following General Formula (I):

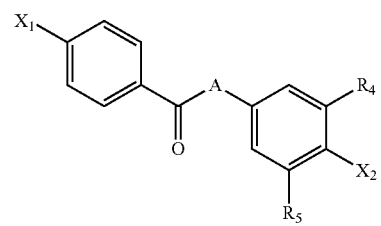

in which:

X1 represents a halogen, a R1, or a G1-R1 group;

A represents a CH=CH group;

X2 represents a G2-R2 group;

G1 and G2, identical or different, represent an atom of oxygen or sulfur;

R1 represents an alkyl or cycloalkyl group having from one to seven carbon atoms, in particular, the alkyl or cycloalkyl group being substituted or not by one or more halogen atoms;

R2 represents an alkyl group substituted by a —COOR3 group, wherein R3 represents a hydrogen atom or an alkyl group having from one to four carbon atoms.

R4 and R5 represent an alkyl group having from one to four carbon atoms.

WO2005/005369 and US20070032543 also disclose the structure and alternative process for the synthesis of compounds according to General Formula (I) as well as to General Formula (II), in particular:

1-[4-trifluoromethylphenyl]-3-[3,5-dimethyl-4-tertbutyloxycarbonyldimethylmethyloxyphenyl]prop-2-en-1-one (compound 57 of US20070032543)

1-[4-trifluoromethylphenyl]-3-[3,5-dimethyl-4-carboxydimethylmethyloxyphenyl]prop-2-en-1-one (compound 58 of US20070032543)

1-[4-trifluoromethyloxyphenyl]-3-[3,5-dimethyl-4-tertbutyloxycarbonyldimethylmethyloxyphenyl]prop-2-en-1-one (compound 61 of US20070032543)

1-[4-trifluoromethyloxyphenyl]-3-[3,5-dimethyl-4-carboxydimethylmethyloxyphenyl]prop-2-en-1-one (compound 62 of US20070032543).

Additional examples of compounds to be used and administered and that can be comprised in compositions according to the invention can be selected from those disclosed in WO2005/073184, and in particular:

1-(4-(Pentylthioethyloxy)phenyl)-3-(4-tert-butyloxycarbonyldimethylmethyloxy-3,5-dimethylphenyl)prop-2-en-1-one, described as compound 1;

1-(4-(Pentylthioethyloxy)phenyl)-3-(4-carboxydimethylmethyloxy-3,5-dimethylphenyl)prop-2-en-1-one, described as compound 2;

1-(4-((R,S)-5-[1,2]dithiolan-3-ylpentyloxy)phenyl)-3-(4-tert-butyloxycarbonyldimethyl methyloxy-3,5-dimethylphenyl)prop-2-en-1-one, described as compound 5;

1-(4-((R,S)-5-[1,2]dithiolan-3-ylpentyloxy)phenyl)-3-(4-carboxydimethylmethyloxy-3,5-dimethylphenyl)prop-2-en-1-one, described as compound 6;

1-(4-Cyclohexylethyloxyphenyl)-3-(4-tert-butyloxycarbonyldimethylmethyloxy-3,5-dimethylphenyl)prop-2-en-1-one, described as compound 10;

1-(4-Cyclohexylethyloxyphenyl)-3-(4-carboxydimethylmethyloxy-3,5-dimethylphenyl)prop-2-en-1-one, described as compound 11;

1-(4-Cyclohexylthioethyloxyphenyl)-3-(4-tert-butyloxycarbonyldimethylmethyloxy-3,5-dimethylphenyl)prop-2-en-1-one, described as compound 22;

1-(4-Cyclohexylthioethyloxyphenyl)-3-(4-carboxydimethylmethyloxy-3,5-dimethyl phenyl)prop-2-en-1-one, described as compound 23;

1-(4-Phenyloxyphenyl)-3-(4-tert-butyloxycarbonyldimethylmethyloxy-3,5-dimethylphenyl)prop-2-en-1-one, described as compound 32;

1-(4-Phenyloxyphenyl)-3-(4-carboxydimethylmethyloxy-3,5-dimethylphenyl)prop-2-en-1-one, described as compound 33.

In a further embodiment of the invention, the compounds as disclosed in WO2005/073184 (herein referred to as compounds of General Formula (III)) that can be used and administered, and that can be comprised in compositions according to the invention have the following General Formula (I):

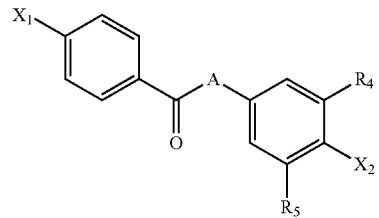

in which:

X1 represents a G1-R1 group;

A represents a CH=CH group;

X2 represents a G2-R2 group;

G1 and G2 represent an atom of oxygen;

R1 represents an cycloalkyl, an aryl or an alkyl group that is substituted or not by one or more alkylthio, cycloalkyl, cycloalkylthio groups or heterocycloalkyl groups or an alkylthio group;

R2 represents an alkyl group substituted by at least a —COOR3 group, wherein R3 represents a hydrogen atom or an alkyl group having from one to four carbon atoms;

R4 and R5 represent an alkyl group having from one to four carbon atoms.

Additional examples of compounds used and administered according to the invention and that can be comprised in compositions according to the invention can be selected from those disclosed in WO2004/005243, WO2004/005233, WO2005/005369, US20070032543 or WO2005/073184, and reduced in the form of the corresponding substituted 1,3-diphenylpropanones.

Accordingly, compounds that can be used and administered according to the invention and that can be comprised in compositions according to the invention can be selected from those disclosed in WO2007/147879, and in particular:

2-[2,6-dimethyl-4-[3-[4-(methylthio)phenyl]-3-oxo-propyl]phenoxy]-2-methylpropanoic acid, described as compound 1;

2-[2,6-dimethyl-4-[3-[4-(methoxy)phenyl]-3-oxo-propyl]phenoxy]-2-methylpropanoic acid, described as compound 6;

2-[2,6-dimethyl-4-[3-[4-(methylthio)phenyl]-3-oxo-propyl]phenoxy]ethanoic acid, described as compound 7;

2-[2,6-dimethyl-4-[3-[4-(propyloxy)phenyl]-3-oxo-propyl]phenoxy]-2-methylpropanoic acid, described as compound 8;

2-[2,6-dimethyl-4-[3-[4-(methylthio)phenyl]-3-oxo-propyl]phenoxy]-2-methyl propanoic acid isopropyl ester, described as compound 13.

In a further embodiment of the invention, the compounds as disclosed in WO2007/147879 (herein referred to as compounds of General Formula (IV)) that can be used and administered and that can be comprised in compositions according to the invention have the following General Formula (I):

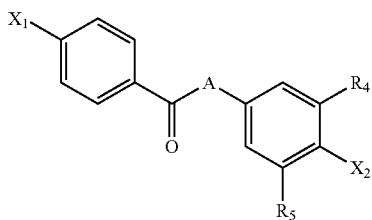

in which:
X1 represents a R1 or a G1-R1 group;
A represents a CH2-CH2 group;
X2 represents a G2-R2 group;
G1 represents an atom of oxygen or sulfur and G2 represents an atom of oxygen;
R1 represents an alkyl or cycloalkyl group having from one to seven carbon atoms;
R2 represents an alkyl group substituted by at least a —COOR3 group, wherein R3 represents a hydrogen atom or an alkyl group having from one to four carbon atoms;
R4 and R5 represent an alkyl group having from one to four carbon atoms.

Similarly to WO2007/147879, WO2007/147880 discloses compounds that can be comprised in compositions according to the invention that correspond to reduced, substituted 1,3-diphenylpropanones derivatives of compounds that were disclosed in WO2004/005243, WO2004/005233, WO2005/005369, US20070032543, or WO2005/073184, and in particular:

2-[2,6-dimethyl-4-[3-[4-(trifluoromethyloxy)phenyl]-3-oxo-propyl]phenoxy]-2-methyl-propanoic acid, described as compound 1;

2-[2,6-dimethyl-4-[3-[4-(trifluoromethylthio)phenyl]-3-oxo-propyl]phenoxy]-2-methyl propanoic acid, described as compound 2;

2-[2,6-dimethyl-4-[3-[4-bromophenyl]-3-oxo-propyl]phenoxy]-2-methylpropanoic acid, described as compound 3;

2-[2,6-dimethyl-4-[3-[4-(trifluoromethyl)phenyl]-3-oxo-propyl]phenoxy]-2-methylpropanoic acid, described as compound 4;

2-[2,6-dimethyl-4-[3-[4-(3,3,3-trifluoropropyloxy)phenyl]-3-oxo-propyl]phenoxy]-2-methyl propanoic acid, described as compound 11;

2-(2,6-dimethyl-4-(3-oxo-3-(4-(2,2,2-trifluoroethoxy)phenyl)propyl)phenoxy)-2-methylpropanoic acid, described as compound 12;

2-(2,6-dimethyl-4-(3-oxo-3-(4-(2,2,2-trifluoroethylthio)phenyl)propyl)phenoxy)-2-methyl propanoic acid, described as compound 13

2-(2,6-dimethyl-4-(3-oxo-3-(4-(trifluoromethoxy)phenyl)propyl)phenoxy)propanoic acid, described as compound 29;

4-(2,6-dimethyl-4-(3-oxo-3-(4-(trifluoromethoxy)phenyl)propyl)phenoxy)-2,2-dimethyl butanoic acid, described as compound 34;

2-(2,6-dimethyl-4-(3-oxo-3-(4-(trifluoromethoxy)phenyl)propyl)phenoxy)-2-methyl propanoic acid tertiobutyl ester, described as compound 35;

2-(2,6-dimethyl-4-(3-oxo-3-(4-(trifluoromethoxy)phenyl)propyl)phenoxy)-2-methyl propanoic isopropyl ester, described as compound 36;

2,2-difluoro-2-(2,6-dimethyl-4-(3-oxo-3-(4-(trifluoromethoxy)phenyl)propyl)phenoxy)acetic acid, described as compound 37.

In a further embodiment of the invention, the compounds as disclosed in WO2007/147880 (herein referred to as compounds according to General Formula (V)) that can be used and administered and that can be comprised in compositions according to the invention have the following General Formula (I):

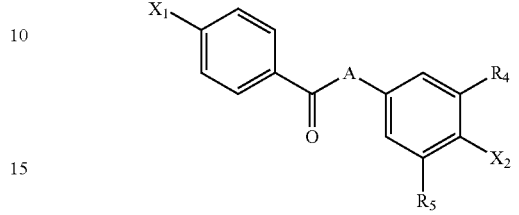

in which:
X1 represents a halogen atom or a R1 or G1-R1 group;
A represents a CH2-CH2 group;
X2 represents a G2-R2 group;
G1 represents an atom of oxygen or sulfur and G2 represents an atom of oxygen;
R1 represents an alkyl or cycloalkyl group that is substituted by one or more halogen atoms;
R2 represents an alkyl group substituted or not by one or more halogen atoms and substituted by at least a —COOR3 group, wherein R3 represents a hydrogen atom or an alkyl group having from one to four carbon atoms.
R4 and R5 represent an alkyl group having from one to four carbon atoms.

The compounds that can be most preferably used and administered according to the invention and comprised in compositions according to the invention are those defined according to General Formula (II), General Formula (IV) or General Formula (V), and in particular:

1-[4-methylthiophenyl]-3-[3,5-dimethyl-4-carboxydimethylmethyloxyphenyl]prop-2-en-1-one (compound 29 of WO2004/005233);

1-[4-methylthiophenyl]-3-[3,5-dimethyl-4-isopropyloxycarbonyldimethylmethyloxyphenyl]prop-2-en-1-one (compound 28 of WO2004/005233);

1-[4-methylthiophenyl]-3-[3,5-dimethyl-4-tertbutyloxycarbonyldimethylmethyloxyphenyl]prop-2-en-1-one (compound 27 of WO2004/005233);

1-[4-trifluoromethylphenyl]-3-[3,5-dimethyl-4-tertbutyloxycarbonyldimethylmethyloxyphenyl]prop-2-en-1-one (compound 57 of US20070032543)

1-[4-trifluoromethylphenyl]-3-[3,5-dimethyl-4-carboxydimethylmethyloxyphenyl]prop-2-en-1-one (compound 58 of US20070032543)

1-[4-trifluoromethyloxyphenyl]-3-[3,5-dimethyl-4-tertbutyloxycarbonyldimethylmethyloxyphenyl]prop-2-en-1-one (compound 61 of US20070032543)

1-[4-trifluoromethyloxyphenyl]-3-[3,5-dimethyl-4-carboxydimethylmethyloxyphenyl]prop-2-en-1-one (compound 62 of US20070032543)

2-[2,6-dimethyl-4-[3-[4-(methylthio)phenyl]-3-oxo-propyl]phenoxy]-2-methylpropanoic acid (compound 1 of WO2007/147879);

2-[2,6-dimethyl-4-[3-[4-(methylthio)phenyl]-3-oxo-propyl]phenoxy]-2-methyl-propanoic acid isopropyl ester (compound 13 of WO2007/147879);

2-[2,6-dimethyl-4-[3-[4-(trifluoromethyloxy)phenyl]-3-oxo-propyl]phenoxy]-2-methylpropanoic acid (compound 1 of WO 2007147880);

2-[2,6-dimethyl-4-[3-[4-(trifluoromethylthio)phenyl]-3-oxo-propyl]phenoxy]-2-methylpropanoic acid (compound 2 of WO 2007147880);

2-(2,6-dimethyl-4-(3-oxo-3-(4-(trifluoromethyloxy)phenyl) propyl)phenoxy)-2-methylpropanoic acid tert-butyl ester (compound 35 of WO 2007147880).

Other compounds that may be used and administered according to the invention and comprised in compositions according to the invention are in particular:

1-[4-methylthiophenyl]-3-[3,5-diisopropyl-4-carboxymethyloxyphenyl]prop-2-en-1-one (compound 74 of US 2007/0032543);

1-(4-Cyclohexylethyloxyphenyl)-3-(4-carboxydimethylmethyloxy-3,5-dimethylphenyl)prop-2-on-1-one (compound 11 of WO 20051073184);

1-[4-isopropylphenyl]-3-[3,5-dimethyl-4-carboxydimethylmethyloxyphenyl]prop-2-en-1-one (compound 56 of US 2007/0032543);

1-[4-methylthiophenyl]-3-[3,5-dimethyl-4-carboxymethyloxyphenyl]prop-2-en-1-one (compound 72 of US 2007/0032543);

1-[4-hexyloxyphenyl]-3-[3,5-dimethyl-4-carboxydimethylmethyloxyphenyl]prop-2-en-1 one (compound 33 of WO 2004/005233);

1-[4-hexylthiophenyl]-3-[3,5-dimethyl-4-carboxydimethylmethyloxyphenyl]prop-2-en-1 one (compound 84 of US 2007/0032543);

1-[4-trifluoromethylthiophenyl]-3-[3,5-dimethyl-4-carboxydimethylmethyloxyphenyl]prop-2-en-1-one (compound 54 of US 2007/0032543);

1-[4-methyloxyphenyl]-3-[3,5-dimethyl-4-carboxydimethylmethyloxyphenyl]prop-2-en-1-one (compound 80 of US 2007/0032543);

1-(4-Phenyloxyphenyl)-3-(4-carboxydimethylmethyloxy-3,5-dimethylphenyl)prop-2-en-1-one (compound 33 of WO 2005/073184);

1-[4-chlorophenyl]-3-[3,5-dimethyl-4-carboxydimethylmethyloxyphenyl]prop-2-en-1-one (compound 17 of WO 2004/005233);

1-[4-bromophenyl]-3-[3,5-dimethyl-4-carboxydimethylmethyloxyphenyl]prop-2-en-1-one (compound 41 WO 2004/005233);

1-[4-trifluoromethylphenyl]-3-[3,5-dimethyl-4-carboxydimethylmethyloxyphenyl]prop-2-en-1-one (compound 58 of US 2007/0032543).

The present invention provides specific uses of compounds of General Formula (I) and related pharmaceutical compositions comprising the same. The compound may or may or not be in the form of a pharmaceutically acceptable salt and is used in a therapeutically effective amount for treating liver disorders Any compound that is defined according to General Formula (II), General Formula (III), General Formula (IV), or General Formula (V), these formulae being encompassed by General Formula (I), can be used in the present invention for treating liver disorders, in particular in the form of a pharmaceutical composition that comprises said compound.

The invention also provides a method for treating liver disorders comprising the administration to a subject in need thereof of a compound of General Formula (I) in which:

X1 represents a halogen, a R1 or G1-R1 group;
A represents a CH=CH or a CH2-CH2 group;
X2 represents a G2-R2 group;

G1 and G2, identical or different, represent an atom of oxygen or sulfur;

R1 represents a hydrogen atom, an unsubstituted alkyl group, an aryl group or an alkyl group that is substituted by one or more halogen atoms, an alkoxy or an alkylthio group, cycloalkyl groups, cycloalkylthio groups or heterocyclic groups;

R2 represents an alkyl group substituted by at least a —COOR3 group, wherein R3 represents a hydrogen atom, or an alkyl group that is substituted or not by one or more halogen atoms, cycloalkyl groups, or heterocyclic groups.

R4 and R5, identical or different, representing an alkyl group that is substituted or not by one or more halogen atoms, cycloalkyl groups, heterocyclic groups.

Compositions comprising compounds wherein X1, X2, A, G1, G2, R1, R2, R3, R4, and R5 are defined according to General Formula (II), General Formula (III), General Formula (IV), or General Formula (V) can also be used to carry out the method for treating liver disorders.

The term "liver disorder" includes any disorder affecting the liver, and in particular any acute or chronic liver disease that involves the pathological disruption, inflammation, degeneration, and/or proliferation of liver cells. In particular, the liver disorder is liver fibrosis, liver cirrhosis, or any other liver disease in which the level in the plasma of some markers of hepatocellular injury, alteration or necrosis, is elevated when compared to normal plasma levels. These biochemical markers associated to liver activity and status can be selected among those disclosed in the literature and in particular Alanine aminotransferase (ALAT), Aspartate aminotransfersase (ASAT), Alkaline Phosphatase (AP), Gamma Glutamyl transpeptidase (GGT), Cytokeratin-18 (CK-18) or Resistin. In a particular embodiment, the liver disorder is a fatty liver disease in which the elevation of one or more of these markers is associated to a more or less significant steatosis in the liver, as it can be confirmed by a liver biopsy. A non-exhaustive list of fatty liver diseases includes NAFLD, NASH, and fatty liver disease associated to disorders such as hepatitis or metabolic syndrome (obesity, insulin resistance, hypertriglyceridemia, and the like).

The term "Hepatoprotection" or "Hepatoprotective" refers to the ability of a compound to reduce, reverse or prevent damage to the liver, in particular by reducing, reversing or preventing the pathological disruption, inflammation, degeneration, and/or proliferation of liver cells such as hepatocytes.

The term "treatment" or "treating" refers to therapy, prevention and prophylaxis of a disorder, in particular of a liver disorder. The treatment involves the administration of a compound or pharmaceutical composition to patient having a declared disorder to cure, delay, or slow down the progress, thus improving the condition of patients. The treatment may be also administered to healthy subjects that are at risk of developing a liver disorder.

Within the context of the invention, the term "subject" means a mammal and more particularly a human. The subjects to be treated according to the invention can be appropriately selected on the basis of several criteria associated to the liver disorder such as previous drug treatments, associated pathologies, genotype, exposure to risk factors, viral infection, as well as any other relevant biomarker that can be evaluated by means of immunological, biochemical, enzymatic, chemical, or nucleic acid detection method. In a particular embodiment, the subject is an overweighed patient (in particular an overweighed prediabetic or diabetic patient) or obese patient suffering from atherogenic dyslipidemia. Indeed, these patients are at risk of developing a liver disorder, in particular NAFLD or NASH. The inventors have shown that compounds as defined above have a beneficial effect on hepatic functions of such patients.

The compounds of General Formula (I) may contain one or several asymmetrical centers. When an enantiomerically pure (or enriched) compound is desired, it can be obtained either by purification of the final product or chiral intermediates, or by asymmetrical synthesis following the typical methods known by one of ordinary skill in the art (for example, by using reactives and chiral catalysts). Some of these compounds can have different stable tautomeric forms. This invention includes the use of stereoisomers (diastereoisomers, enantiomers), pure or mixed, as well as racemic mixtures and geometrical isomers of compounds of General Formula (I).

The compounds of General Formula (I) can be formulated as "pharmaceutically acceptable" salts, being slightly- or non-toxic salts obtained from organic or inorganic bases or acids of compounds of General Formula (I). These salts can be obtained during the final purification step of the compound or by incorporating the salt into the previously purified compound.

The pharmaceutical compositions comprising a compound of General Formula (I) for the treatment of liver disorders can comprise one or several excipients or vehicles, acceptable within a pharmaceutical context (e.g. saline solutions, physiological solutions, isotonic solutions, etc., compatible with pharmaceutical usage and well-known by one of ordinary skill in the art). These compositions can comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, carboxymethylcellulose, polysorbate 80, mannitol, gelatin, lactose, vegetable oils, acacia, liposomes, etc. These compositions can be formulated in the form of injectable suspensions, gels, oils, pills, suppositories, powders, gel caps, capsules, aerosols, etc., eventually by means of galenic forms or devices assuring a prolonged and/or slow release. For this kind of formulation, agents such as cellulose, carbonates or starches can advantageously be used.

The compounds of General Formula (I) should be administered in an effective quantity of a compound by using a pharmaceutical composition as above-defined. Within the context of the invention, the term "an effective quantity" refers to an amount of the compound sufficient to produce the desired therapeutic result.

The compounds of General Formula (I) can be administered in different ways and in different forms that allow administering said compounds in a therapeutically effective amount. Thus, for example, they can be administered in a systematic way, per os, parenterally, by inhalation, or by injection, such as for example intravenously, by intra-muscular route, by subcutaneous route, by transdermal route, by intra-arterial route, etc. Oral administration is the preferential route of administration for pharmaceutical compositions comprising a compound of General Formula (I) for the treatment of liver disorders.

The frequency and/or dose relative to the administration can be adapted by one of ordinary skill in the art, in function of the patient, the pathology, the form of administration, etc. Typically, the compounds of General Formula (I) can be administered for the treatment of liver disorders at doses varying between 0.01 mg and 1 g per administration, preferentially from 1 mg to 100 mg per administration. Administration can be performed daily or even several times per day, if necessary.

The compounds and compositions of the invention can be advantageously administered in combination with other therapeutic agents, currently available in the market or in development for the treatment of metabolic and/or liver disorders, such as metformin, insulin, thiazolidinediones, glitazones, statins, inhibitors of cholesterol and/or other lipid lowering drugs.

In a further embodiment, the present invention provides methods of treating liver disorders comprising the administration of a compound of General Formula (I), in particular in the form of pharmaceutical compositions containing these compounds. Such methods may comprise the administration of any compound that is defined according to General Formula (II), General Formula (III), General Formula (IV), or General Formula (V).

The compounds and compositions of the invention provide advantageous therapeutic tool for the treatment of liver disorders, and in particular fatty liver diseases including NAFLD and NASH, due to the hepatoprotective effects of the compounds of General Formula (I). In particular, these compounds can be selected amongst those in which X1, X2, A, G1, G2, R1, R2, R3, R4, and R5 are defined according to General Formula (II), General Formula (III), General Formula (IV), or General Formula (V). A further object of the present invention relates to a compound of General formula (I) as described above, and in particular of General Formula (II), (Ill), (IV) and (V), for use in a method of treating liver disorders. In a particular embodiment, specific liver disorders intended to be treated are those described above such as liver fibrosis or a fatty liver disease. In yet another embodiment, the compounds for use in said methods are those specifically described above.

In general, the liver-specific properties of compounds of General Formula (I) can be evaluated in specific patient populations presenting a liver disorder such as NAFLD and/or NASH at inclusion. For example, a double blind, placebo-controlled and randomized study can evaluate the efficacy of oral administration of the compound (at the dose of 80 mg/day or more) during 3-12 months in subjects that have been diagnosed for NAFLD (steatosis only) and/or NASH (steatosis and fibrosis) and present elevated aminotransferases levels. Any statistically relevant improvement on main biochemical parameters (such as reduction of aminotransferases, GGT, and/or Cytokeratin-18 levels and/or reduction of Resistin levels), on volume of hepatic steatosis measured by imaging technique or on histological features of liver biopsies (measurement of steatosis, liver inflammation and fibrosis) can be regularly assessed in these patients during the study (on a monthly or more frequent basis). Additional parameters such as total/LDL-/HDL-cholesterol, hemodynamic parameters, Body Mass Index, insulin resistance, markers of inflammatory or oxidative stress, plasma insulin and glucose, markers of renal function in urine, hepatic imaging by MRI, and/or histomorphology in liver biopsies can be also measured during the study and/or at the end of the study for completing the efficacy profile of compounds for treating of liver disorders.

All references cited herein are fully incorporated by reference in their entirety. Having now fully described the invention, it will be understood by those of ordinary skill in the art that the invention may be practiced within a wide and equivalent range of conditions, parameters and the like, without affecting the spirit or scope of the invention or any embodiment thereof. Several other advantages of the inven-

EXAMPLES

Example 1

Effects of Compounds of General Formula (I) on Liver-Specific Biochemical Indexes Materials & Methods 1-[4-methylthiophenyl]-3-[3,5-dimethyl-4-carboxydimethylmethyloxyphenyl]prop-2-en-1-one (Cpd 29 of WO2004/005233) has been formulated as hard shell capsules containing 5, 10 or 20 mg of the compound. The compound (80 mg) was administered orally once daily for 28 days. The study has been performed in two parallel groups in double-blind conditions: placebo or Cpd 29 of WO2004/005233.

The tolerability and safety of once-a-day administrations, as well as the efficacy in improving plasma lipids and glucose homeostasis compared with placebo, were evaluated in two pilot trials using relevant biochemical parameters. The data were used to calculate the percentage of change due to the compound when compared to the placebo after 28 days of treatment.

Results & Conclusions:

A first pilot, double-blind, placebo controlled, randomized study has been performed in patients suffering from atherogenic dyslipidaemia and abdominal obesity for assessing the tolerability and safety of once-a-day administrations of oral doses of Cpd 29 of WO2004/005233 (at the dose of 80 mg/day), as well as the efficacy on plasma triglycerides and HDL-cholesterol (primary objectives).

Relative to the placebo group, the therapeutic efficacy of this compound was demonstrated with a statistically significant 21% ($p<0.01$) reduction of plasma triglycerides and a 9% ($p<0.01$) increase in good cholesterol (HDL-C) level. These metabolic effects were comparable to those published with the fibrates in the same patient population. Furthermore, the compound revealed a remarkable lack of effect on Homocystein (a known cardiovascular risk factor). The compound showed significant effects on multiple secondary evaluation criteria including reduction of liver acute phase inflammation markers such as fibrinogen and haptoglobin ($p<0.01$). Effects on biochemical parameters of liver function were also measured and the administrations of oral doses of Cpd 29 of WO2004/005233 led unexpectedly to a statistically significant 23% reduction of Gamma Glutamyl transpeptidase level ($p<0.001$) and a 13% reduction of Alanine aminotransferase level ($p<0.01$).

A second pilot, double-blind, placebo controlled, randomized study has been performed in patients suffering from impaired fasting glucose, impaired glucose tolerance and abdominal obesity for assessing the tolerability and safety of once-a-day administrations of oral doses of Cpd 29 of WO2004/005233 (at the dose of 80 mg/day), as well as the efficacy on glucose and lipid metabolism.

Relative to the placebo group, the therapeutic efficacy of this compound was demonstrated with a statistically significant reduction of fasting plasma glucose (−5%, $p<0.05$), of fasting insulinemia (−25%, $p<0.01$) and of insulin resistance index, HOMA-IR (−31%, $p<0.01$). In parallel, Cpd 29 of WO2004/005233 reduced plasma triglycerides (−25%, $p<0.001$) and LDL-C while enhancing HDL-C (+9%, $p<0.01$). The compound showed significant effects on multiple secondary evaluation criteria including reduction of liver acute phase inflammation markers such as haptoglobin ($p<0.01$). Biochemical parameters on liver function were also calculated and the administrations of oral doses of Cpd 29 of WO2004/005233 led to a statistically 15% reduction of Gamma Glutamyl transpeptidase level ($p<0.01$).

These results demonstrated that an oral formulation of a compound of General Formula (I) not only is well tolerated by patients but has positive effects on multiple biochemical parameters associated with NAFLD and NASH including liver enzymes, insulin sensitivity, lipid metabolism, and liver inflammation markers. In particular, Cpd 29 of WO2004/005233 significantly decreases plasma levels of ALAT and GGT, two common specific biomarkers of liver dysfunction which are elevated in patients suffering from NAFLD and NASH.

Example 2

Animal Models for Testing Liver-Specific Properties of Compounds of General Formula (I)

Materials & Methods

Animal Model and Treatment: ob/ob Mice

Male ob/ob mice (8 weeks of age) were purchased from Charles River (L'Arbresle, France) and were kept on a 12-hour light/dark cycle at a constant temperature of 20±3° C. After a 1 week acclimation, mice were separated in groups of 8 animals selected such that the distribution of their body weight and their 6 hours fasting glycemia determined before the experiment were uniform. Animals were fed a standard chow diet (R03, SAFE) and treated during 26 days with the compounds of interest. Compounds, including the Compound 29 of WO2004005233 (Cpd 29, at 10 or 30 mg/kg/day), Fenofibrate (100 mg/kg/day) and Rosiglitazone (10 mg/kg/day) were administered daily by gavage. Control animals were treated with vehicle only (Carboxymethylcellulose 1%+Tween-80 0.1%). Animals had access to food and water ad libitum.

Animal Model and Treatment: Study in hApoE2 Knock-in Mice

Female hApoE2 knock-in (KI) transgenic mice (Sullivan et al., 1998)(4 weeks of age). Mice were kept on a 12-hour light/dark cycle at a constant temperature of 20±3° C. After a 1 week acclimation, mice were separated in groups of 7-10 animals selected such as the distribution of their body weight and plasmatic lipid levels determined before the experiment were uniform. Animals were fed a Western diet (20% saturated fat and 0.2% cholesterol, Harlan Teklad TD88137) at weaning and during 12 weeks. Compounds of interest (Cpd 29 at 0.3 mg/kg/day and Fenofibrate at 100 mg/kg/day) were incorporated in the Western diet (SAFE, Augy, France) and administrated to mice during 12 weeks. Control animals received Western diet only. Animals had access to food and water ad libitum.

Animal Model and Treatment: Studies in hApoE2 KI and hApoE2 KI PPARalpha KO Mice Female hApoE2 knock-in (KI) and hApoE2 KI/PPARalpha knock-out (KO) age-matched transgenic mice (8 to 25 weeks of age for the first experiment and 10 to 14 weeks of age for the second experiment. hApoE2 KI/PPARalpha KO mice were generated by crossing of homozygous hApoE2 KI mice (Sullivan P et al., 1998) and homozygous PPARalpha deficient mice (Lee et al., 1995). Mice were kept on a 12-hour light/dark cycle at a constant temperature of 20±3° C. After a 1 week acclimation, mice were separated in groups of 4-6 animals selected such that the distribution of their age, body weight and plasmatic lipid levels determined before the experiment were uniform. Animals were fed a Western diet (20% saturated fat and 0.2% cholesterol, Harlan Teklad TD88137) during 2 weeks in the first study, that involved the daily administration of Cpd 29 (at 30 mg/kg/day by oral gavage), and during 6 weeks in the second study, that involved the daily administration of Compound 1 of WO2007147879 (Cpd1, at 30 mg/kg/day by oral gavage). Control animals were treated with vehicle only (Carboxymethlycellulose 1%+Tween-80 0.1%). Animals had access to food and water ad libitum.

Preparation of Biological Samples Obtained from Animal Models

At the end of the studies, the animals were weighed and sacrificed under anesthesia. Blood was collected from the retro-orbital sinus; plasma was obtained by centrifugation (4 000 rpm, at 4° C. for 15 min) and subsequently frozen and stored at −20° C. Tissues and livers were isolated and snap-frozen in liquid nitrogen and stored at −80° C. for subsequent analysis (gene expression and biochemistry) or fixed in 4% paraformaldehyde for histology.

Plasma Analysis

Alanine aminotransferase levels were determined in plasma using the RX Daytona™ automatic analyzer (Randox) and the appropriate dosage kit (Randox, cat# AL 3801).

Gene Expression Analysis

Total RNA was isolated from frozen livers using the NucleoSpin® 96 RNA kit (Macherey Nagel), according to the manufacturer's instructions. Reverse transcription was performed on 1 μg of total RNA by action of 1 μl of MMLV-RT enzyme (Invitrogen) during 1 hour at 37° C. in a total volume of 30 μl. The reaction conditions were 1× buffer (Invitrogen), 1.5 mM DTT (Invitrogen), 0.18 mM dNTPs (Promega), 200 ng pdN6 (Amersham), 30 U RNase inhibitor (Promega). Quantitative PCR was then carried out using the MyiQ Single-Color Real-Time PCR Detection System (Biorad). Briefly PCR reactions were performed in 96 well plates on 5 μl of diluted reverse transcription mix using the iQ SYBR Green Supermix kit. The reaction conditions were: 25 μl of volume reaction, 3 mM of MgCl2, and 0.5 μl of each reverse and forward primer solutions (10 pMol), Tm of 60° C. The pairs of primers that have been designed for the specific amplification of each target genes are summarized in Table 1.

TABLE 1

| Genes | Reverse primer (5'-3') | Forward primer (5'-3') |
|---|---|---|
| 36B4 | GGGAAGGTGTAATCCGTCTC CACAG (SEQ ID NO: 1) | CATGCTCAACATCTCCCCCTTC TCC (SEQ ID NO: 2) |
| TNF alpha | AGGTACAACCCATCGGCTGG (SEQ ID NO: 3) | CGTCGTAGCAAACCACCAAGTG (SEQ ID NO: 4) |
| TGF beta | TGGTTGTAGAGGGCAAGGAC (SEQ ID NO: 5) | TTGCTTCAGCTCCACAGAGA (SEQ ID NO: 6) |
| CCL5 | CACACTTGGCGGTTCCTTCG (SEQ ID NO: 7) | CCCTCACCATCATCCTCACTGC (SEQ ID NO: 8) |
| Col1a1 | GCCAGGAGAACCAGCAGAG (SEQ ID NO: 9) | AGGCGAACAAGGTGACAGAG (SEQ ID NO: 10) |

The quantity of fluorescence emitted is directly proportional to the quantity of complementary DNA present at the start of the reaction and amplified during the PCR. The relative levels of expression were determined using the standard curve for each transcript. The results were then normalized in regard to the signals obtained with the 36B4 control (a reference transcript for hepatic gene expression). The induction factor, i.e. the ratio between the relative signal induced by the compound according to the invention and the average of the values relating to the control group, was then calculated for each sample. The higher this factor, the more the compound promotes target gene expression. The final result is depicted as the average of the induction values in each experimental group.

Histological Analysis of Liver

Formalin-fixed liver tissue was processed, and 5-μm-thick paraffin sections were stained with Hematoxylin and Eosin. The histological analysis of stained liver sections was carried out in blind conditions to quantify liver steatosis and liver intralobular inflammation. Liver steatosis was scored from 0 to 3 as follows: 0 (very slightly affected), 1 (slightly affected), 2 (moderately affected), 3 (highly affected). Liver intralobular inflammation was also scored depending on the number of inflammatory foci counted by field of observation as follows: 0 (<1 focus/field), 1 (1 to 2 foci/field), 2 (2 to 4 foci/field) 3 (more than 4 foci/field).

Hepatic Lipid Analysis

Approximately 100 mg of frozen liver tissue were homogenized with a tissue homogenizer (Precellys®24, Bertin Technologies, France) in 150 mM NaCl buffer, containing 15.4 mM NaN3. Lipid fractions in homogenates were extracted with chloroform-methanol (2:1, v/v) followed by measurement of the total cholesterol (using the Cholesterol RTU™ 61218 kit, Biomerieux, France) and true triglycerides (TR0100 kit, Sigma-Aldrich).

Results & Conclusions

Several animal models are disclosed in the literature as reflecting the etiology, disease progression, and the pathology of human liver diseases. However, these models do not always display the range of histo-pathological and patho-physiological features associated with specific liver diseases. As recently reviewed (Fan J and Qiao L, 2009), this is particularly evident in the case of NAFLD or NASH, wherein genetic (in transgenic mice), nutritional (in rats or mice), or mixed models have been established.

NASH is characterized by pathological alterations of liver ranging from steatosis and liver inflammation to liver degeneration, fibrosis and cirrhosis. The pathogenesis of NASH remains poorly understood. It is a component of the metabolic syndrome and therefore frequently associated with hyperlipidemia. Different transgenic animal models were used to characterize the effects of exemplary compounds of the General Formula (I), and more specifically of General formula (I) and General Formula (IV): the insulin-resistant, leptin deficient ob/ob mice and the dyslipidemic hApoE2 knock-in mice (the latter one, with or without a further genomic modification consisting in the inactivation of PPA-Ralpha gene).

Leptin deficient ob/ob mice are obese, dyslipidemic, insulin resistant and develop hepatic injury and steatosis. Hepatic steatosis is relatively asymptomatic but individuals with this disorder are at greater risk for developing NASH. This first protocol was designed to analyze the effects of the Cpd 29 and of the reference compounds Fenofibrate and Rosiglitazone on the early stages of NASH, i.e. inflammation in the steatosis liver of ob/ob mice. In ob/ob mice, 26 days of treatment with the Rosiglitazone induced the increase of the hepatic expression of TNFalpha in the ob/ob mice while no major change in the expression of this cytokine was observed in animals treated with the Fenofibrate. On the contrary, the administration of Cpd 29 inhibited the expression of this cytokine in a dose-response manner (FIG. 2A). Following the same treatment, the hepatic expression level of TGFbeta was equivalent in all control and reference groups (control, Fenofibrate and Rosiglitazone). Again, the administration of Cpd 29 inhibited the expression of this growth factor in a dose-response manner, an effect that is more statistically relevant when Cpd 29 was administered at 30 mg/kg/day (FIG. 2B).

Plasma ALAT was measured as a surrogate marker for assessing liver injury in these ob/ob mice after the 26 days of treatment with the different compounds. When the level of plasma ALAT is compared with either the control group or the Fenofibrate-treated group, the group of mice that were treated with Rosiglitazone exhibited a significant increase of their plasmatic levels of ALAT. On the contrary, the administration of Cpd 29 at 30 mg/kg/day induced a statistically significant decrease of plasmatic levels of ALAT (FIG. 2C). Another in vivo model was used in order to study the effects of Cpd 29 and of the reference compound Fenofibrate on physiological parameters normally being considered as relevant for assessing NASH. In "humanized" ApoE2 knock-in mice (referred as hApoE2 KI) the human ApoE2 allele replaces the murine apoe gene, so that these mice express human ApoE2 (hApoE2) under the control of the endogenous promoter sequences at physiological levels. However, hApoE2 has a markedly reduced affinity for the LDL receptor, leading to a plasma lipoprotein profile resembling human type III hyperlipoproteinemia (Sullivan et al., 1998). Similar to humans, hApoE2 KI mice are responsive to lipid-lowering drugs such as fibrates (ligands for PPARα). This class of drugs has been shown to reverse steatohepatitis in mice (Shiri-Sverdlov R et al., 2006) and thus this model can allow evaluating liver-specific anti-inflammatory and anti-fibrotic effects of compounds of General Formula (I). In particular, elevated TNFα levels are related to liver inflammation, necrosis and fibrosis typical of NASH (Larter et al., 2008). TGF is a peptide found in many cell types that regulates wound healing and apoptosis. The isoform found in hepatic cells, TGFβ1, has been found in many models of hepatic fibrosis and levels increase in chronic active hepatitis and fibrotic alcoholic liver disease (Nan et al., 2009).

The different hApoE2 KI mice were treated during 12 weeks while fed a Western diet. In this model, Cpd 29 inhibited the hepatic expression of gene that are relevant for liver inflammation (TNFα, CCL5, TGFβ; FIGS. 3A, 3B, 3C respectively) with an efficacy similar (if not superior) to Fenofibrate that was administered at an higher dose.

However, the mice group treated with Cpd 29 showed a statistically significant inhibition of the expression of genes like those for specific collagen chains that are involved in liver fibrosis (Basaranoglu et al., 2010), and in particular Col1a1 (FIG. 3D). Such an effect on collagen genes was not observed in the mice group treated with Fenofibrate. These results demonstrate that Cpd29 displays anti-inflammatory and anti-fibrotic properties in an in vivo model of NASH.

Exemplary compounds of the General Formula (I) were tested in vivo in a high fat diet mice model. hApoE2 KI and hApoE2 PPARalpha KO ("humanized" ApoE2 knock-in mice deficient for the mPPARalpha gene) were fed a Western diet and daily treated with the Cpd 29 at 30 mg/kg/day during 2 weeks. At the end of the protocol, liver steatosis and intralobular inflammation were evaluated in the control and treated mice by means of histological analysis and specific scores.

This study demonstrated that the treatment with Cpd 29 inhibits the development of both liver steatosis and liver inflammation that is induced by the diet in hApoE2 KI mice and, even more rapidly in hApoE2 KI/PPARalpha KO mice, wherein it is evident an acceleration of the liver disorder due to the lack of PPARalpha (Table 2 and Table 3).

TABLE 2

| Liver Steatosis (score) | hApoE2 KI | | hApoE2 KI/PPARalpha KO | |
|---|---|---|---|---|
| | Vehicle | Cpd 29 (30 mg/kg/day) | Vehicle | Cpd 29 (30 mg/kg/day) |
| 0 | 17% | 83% | 0% | 0% |
| 1 | 50% | 17% | 33% | 33% |
| 2 | 33% | 0% | 33% | 50% |
| 3 | 0% | 0% | 33% | 17% |

TABLE 3

| Liver Inflammation (score) | hApoE2 KI | | hApoE2 KI/PPARalpha KO | |
|---|---|---|---|---|
| | Vehicle | Cpd 29 (30 mg/kg/day) | Vehicle | Cpd 29 (30 mg/kg/day) |
| 0 | 50% | 100% | 17% | 67% |
| 1 | 50% | 0% | 33% | 17% |
| 2 | 0% | 0% | 33% | 17% |
| 3 | 0% | 0% | 17% | 0% |

In another study, the liver-specific anti-inflammatory and anti-fibrotic properties effects of Cpd 29 and Compound 1 of WO2007/147879 (Cpd 1) were evaluated in the hApoE2 KI/PPARalpha KO mice that were fed a Western diet and daily treated with the selected compounds during 6 weeks.

Both Cpd 29 and Cpd 1 inhibited the liver expression of TNFα, TGFβ and collagen in hApoE2 KI/PPARalpha KO mice (FIGS. 4A, 4B, and 4C, respectively), confirming the liver-specific (mainly PPARalpha-independent), anti-inflammatory, and anti-fibrotic properties of these compounds in a relevant in vivo model for NASH. The hepatic lipids analysis further revealed that both Cpd 29 and Cpd 1 prevented the triglycerides accumulation in the liver of hApoE2 KI/PPARalpha KO mice (FIG. 4D).

Taken all together, those results highlighted the liver-specific anti-inflammatory, anti-steatosis and anti-fibrotic properties of the Compound 29 of WO2004/005233 (comprised in General Formula I and II) and the Compound 1 of WO2007/147879 (comprised in General Formula (I) and (IV)) in vivo.

Additional model for testing the compounds of General Formula (I) are nutritional animal models of NASH such as the methionine- and choline-deficient (MCD) model which is based on a diet containing high sucrose and fat but lacks two components, methionine and choline that are essential factors for liver metabolism. Mice or rats fed on this diet rapidly develop hepatic inflammation, which further evolves into steatosis, necrotic inflammation, fibrosis, and oxidative stress. This approach has been used to show the potential therapeutic effects on liver steatosis, fibrosis, oxidative stress, and/or inflammation that are associated to the administration of compounds such as Rosiglitazone (Tahan V., et al. 2007), the pan-caspase inhibitor VX-166 (Witek R et al., 2009), Zeaxantin (Chamberlain S et al., 2009), Telmisartan (Kudo H et al., 2009) or Wy-14,643 (Ip E et al., 2004).

The compounds of General Formula (I) can be tested in an MCD model established in Sprague Dawley rats (8 weeks old) or C57Bl6 mice that are fed with the methionine- and choline-deficient diet during 4 to 12 weeks. Treatment with the compounds of interest, including compounds that are chosen as negative or positive control, are then administered daily at different doses to groups of ten or more animals by gavage during the following 4 to 12 weeks. Several types of measurements can be performed before, during, or at the end of the treatment, with or without sacrificing the animals. Biochemical dosages (aspartate aminotransferase and alanine aminotransferase activities, total bilirubin, alkaline phosphatase, LDL/HDL-cholesterol, serum hyaluronate, hepatic triglyceride and plasmatic triglyceride) and histomorphometric analysis (for determining the liver area presenting fibrosis and/or steatosis) are the more relevant measurements. The dosage of inflammatory markers (such as Interleukins-1a, -1b, -2, -4, -6, -10, Interferon gamma, or TNFalpha) and/or of the expression of relevant genes (such as type I collagen or liver-specific chemokine receptors) can be also evaluated.

Alternatively, animal models based on the chemically-induced hepatic fibrosis can be used for studying the anti-fibrotic effect of the compounds of General Formula (I). For example the administration of thioacetamide (TAA) or carbon tetrachloride (CCL4) induces an increase in reactive oxygen species (ROS) promoting lipid peroxidation, hepatic stellate cell proliferation and collagen hyperproduction, leading to chronic liver injury and fibrosis in rats. This approach has been used to show the positive effect on liver fibrosis, oxidative stress, and/or inflammation with compounds such as Curcumin (Fu Y et al., 2008) or Pioglitazone (Yuan G et al., 2004).

The compounds of General Formula (I) can be tested in an CCL4 model that is established in Sprague Dawley rats (8 weeks old) which receive increasing doses of CCL4 intraperitoneally diluted in liquid paraffin (of 50%) every five days for 4 to 12 weeks. Phenobarbital can be also administered starting from 10 days before the first dose of CCL4 in order to potentiate the model. Treatment with the compounds of interest, including compounds that are chosen as negative or positive control, are then administered daily at different doses (comprised between 0.01 and 100 mg/kg/day) to groups of ten or more rats by gavage during the following 4 to 12 weeks. As in the MCD model, several types of measurements can be performed before, during, or at the end of the treatment, with or without sacrificing the rats, for evaluating the efficacy of the treatment on the basis of biochemical dosages and histomorphometric analysis, in association to hemodynamic indexes and the dosage of inflammatory markers and/or of the expression of relevant genes.

The animal models described above allow comparing liver-specific activities of compounds of General Formula (I) among them and with compounds already known as having liver-specific (and in particular NAFLD-/NASH-specific) therapeutic properties. In particular, the data shown in this Example suggest the superiority of compounds of General Formula (I) when compared to reference compounds.

Example 3

In Vitro/Ex Vivo Models for Testing Liver-Specific Properties of Compounds of General Formula (I)

Some in vitro/ex vivo models have been established for screening compounds that can have a positive effect on liver fibrosis, oxidative stress, and/or liver inflammation. In fact, a key event in liver fibrosis is the activation of hepatic stellate cells (HSC). After hepatocyte damage, this cell type becomes activated and starts to proliferate (Sato M et al., 2003). Activated HSCs (for example, rat or human HSC isolated from livers or rat HSC-T6 cell line) can be activated and produce excessive amounts of extracellular matrix compounds and inhibitors of matrix degradation. This approach has been used to show the positive effect of compounds such as curcumin (Xu et al., 2003), thiazolidinediones (Miyahara T et al., 2000), or 17beta-estradiol (Liu Q et al., 2004).

The in vitro/ex vivo models described above allow comparing liver-specific activities of compounds of General Formula (I) among them and with compounds known as having liver-specific (and in particular NAFLD-/NASH-specific) therapeutic properties.

Example 4

Effects of Compounds of General Formula (I) on Pathways Responsible for Fibrosis The inventors have also conducted experiments with other compounds of General Formula (I) showing that said compounds are able to act on pathways responsible for fibrosis, which is a key feature of a number of liver disorders, in particular NAFLD, NASH and cirrhosis. These experiments are summarized in table 4.

Materials & Methods

Compounds were dissolved in dimethyl sulfoxide (DMSO, Fluka cat#41640)

hHSC Culture and Treatment Conditions

The human primary hepatic stellate cells (hHSC) (ScienCell) were cultured in STeCM medium (ScienCell cat#5301) that was supplemented with 2% fetal bovine serum (FBS, ScienCell cat#0010), 1% penicillin/streptomycine (ScienCell cat#0503) and stellate cell growth supplement (SteCGS; ScienCell cat#5352). Culture plastics were coated with Poly-L Lysine (Sigma cat# P4707).

Determination of PDGF-Induced Proliferation hHSC were plated at a density of $1.2 \times 10^4$ cells/well into 96-well plates and were cultured overnight at 37° C. and 5% $CO_2$, followed by washing of cells with PBS (Invitrogen cat#14190) and replacing the growth medium with a serum-free and SteCGS-free medium for an additional 24 hours. For PDGF-induced proliferation assay, cells were pre-treated with a compound of General Formula (I) for 1 hour before the addition of PDGF-BB (10 ng/ml; R&D Systems cat#520-BB). Treatments were then continued for additional 20 hours.

Cell proliferation was measured by bromodeoxyuridine (BrdU) incorporation using a BrdU labeling and detection kit (Roche cat#11647229001). BrdU labeling solution was added to cells, followed by incubation for another 4 hours before fixation, addition of nucleases, addition of anti-BrdU-POD and peroxidase substrate. The absorbance at 405 nm (with a reference wavelength at 690 nm) was measured using an ELISA plate reader (Tecan).

HSC Activation with TGF-$\beta$1

The human primary hepatic stellate cells (hHSC) (ScienCell) were cultured under standard conditions, as described above. For experiments to determine gene expression patterns, hHSC were plated at a density of $7 \times 10^4$ cells/well into 24-well plates and were cultured overnight. Next day, culture medium was replaced by serum-free and SteCGS-free medium for an additional 16 hours. Cells were treated with a compound of General Formula (I) in addition to TGF$\beta$1 (1 ng/ml) in a serum-free and SteCGS-free medium for 24 hours.

Gene Expression

Total RNA was isolated using Nucleospin® 96 RNA kit (Macherey Nagel) following manufacturer's instructions. 100 ng of total RNA were reverse transcribed in cDNA using MMLV RT (Moloney Murine Leukemia Virus Reverse Transcriptase) (Invitrogen cat#28025) in presence of RT buffer 1× (Invitrogen), 1 mM DTT (Invitrogen), 0.18 mM dNTPs (Promega), 200 ng pdN6 (Amersham) and 30 U of RNase inhibitor (Promega).

Quantitative PCR was then carried out using the CFX96 TOUCH™ Real-Time PCR Detection System (Biorad). Briefly, PCR reactions were performed in 96 well plates on 5 µl of 5× diluted reverse transcription mix using the iQ SYBR Green Supermix kit. The experimental conditions were: 25 µl of volume reaction, 3 mM of MgCl2, and 0.5 µl each of reverse and forward primers (10 pMol).

TABLE 4

| Primer name | Sequence (5'→3') |
|---|---|
| αSMA forward | ACTGCCTTGGTGTGTGACAA (SEQ ID NO: 11) |
| αSMA reverse | TGGTGATGATGCCATGTTCT (SEQ ID NO: 12) |
| Col1α1 forward | AATGGTGCTCCTGGTATTGC (SEQ ID NO: 13) |
| Col1α1 reverse | ACCAGGTTCACCGCTGTTAC (SEQ ID NO: 14) |
| Col4α1 forward | GTTGGTCTACCGGGACTCAA (SEQ ID NO: 15) |
| Col4α1 reverse | GTTCACCTCTGATCCCCTGA (SEQ ID NO: 16) |

Expression levels were normalized using the expression of 36B4 gene as reference (sequences SEQ ID NO:1 and SEQ ID NO:2 as shown above).

For each gene, the standard curves were drawn by selecting the best points (at least three points) in order to have PCR reaction efficiency close to 100% and a correlation coefficient close to 1. Expression levels were determined using the standard curve equation for both the housekeeping gene and the target gene (taking into account the specific PCR efficiency of each target gene).

TABLE 5

| | Inhibition of the TGFβ1-induced hHSC activation by compounds of formula (I) at 10 μM | | | Inhibition of the PDGF-BB-induced hHSC proliferation by compounds of formula (I) at 10 μM BrdU Incorporation |
|---|---|---|---|---|
| | αSMA | Col1α1 | Col4α1 | |
| Cpd 74 US20070032543 | −97%*** | −82%*** | −85%*** | −127%*** |
| Cpd 11 WO2005073184 | −92%*** | −66%** | −78%*** | −6% |
| Cpd 56 US20070032543 | −87%*** | −62%** | −66%*** | −127%*** |
| Cpd 72 US20070032543 | −74%*** | −37% | −51%*** | −126%*** |
| Cpd 33 WO2004OO5233 | −71%*** | −58%* | −73%*** | 35% |
| Cpd 84 US20070032543 | −64%*** | −60%** | −64%*** | −33% |
| Cpd 54 US20070032543 | −57%*** | −27% | −40%*** | 12% |
| Cpd 80 US20070032543 | −55%*** | −64%** | −66%*** | −136%*** |
| Cpd 33 WO2005073184 | −49%*** | −37% | 12% | −127%*** |
| Cpd 17 WO2004OO5233 | −30%*** | −29% | −56%*** | 6% |
| Cpd 41 WO2004OO5233 | −2% | −28% | −32%** | −34% |
| Cpd 58 US20070032543 | 5% | 55%* | −3% | −5% |

REFERENCES

Angulo P et al., 2002. Best Pract Res Clin Gastroenterol; 16: 797-810.
Basasaranoglu, M et al., 2010. World J Gastroenterol; 16: 2223-6.
Chamberlain S et al., 2009. Dig Dis Sci; 54: 1460-4.
Dowman J. K et al., 2010, Q J Med; 103: 71-83
Fan J and Qiao L, 2009. Hepatobil Pancrat Dis Int; 8: 233-240.
Fu Y et al., 2008. Mol Pharmacol; 73: 399-409.
Gressner A et al., 2009. World J Gastroenterol; 15: 2433-2440.
Ip E et al., 2004. Hepatology; 39: 1286-96.
Kudo H et al., 2009. Liver Int; 29: 988-96.
Larter C et al., 2008. J Gastroenterol Hepatol; 23: 1635-48.
Lee S et al., 1995. Mol Cell Biol; 15: 3012-22.
Liu Q et al., 2004. World J Gastroenterol; 10: 1315-20.
Marchesini G et al. 2003. Hepatology; 37:917-923.
Miyahara T et al., 2000. J Biol Chem; 275: 35715-22.
Nan Y et al., 2009. Scand J Gastroenterol, 44, 1121-31.
Nelson A et al., 2009. J Clin Gastroenterol; 43: 990-994
Neuschwander-Tetri et al., 2003. Hepatology; 38: 1008-1017.
Sato M et al., 2003. Cell Struct Funct; 28: 105-12.
Shiri-Sverdlov R et al., 2006. J Hepatol; 44: 732-41.
Sullivan P et al., J Clin Invest; 102: 130-5.
Tahan V et al., 2007 Dig Dis Sci; 52: 3465-3472.
Vuppalanchi R and Chalasani N, 2009. Hepatology; 49: 306-317.
Witek R et al., 2009. Hepatology; 50:1421-30.
Xu et al., 2003. Am J Physiol Gastrointest Liver Physiol; 285: G20-G30.
Yeh M et al., 2007. Am J Clin Pathol; 128:837-847.
Yuan G et al., 2004. World J Gastroenterol; 10: 1047-51.

We claim:

1. A method for the treatment of a liver disease selected from an alcohol-related liver disease, a viral liver disease and an immune-mediated liver disease in a subject in need thereof, comprising administering to the subject a compound of General Formula (I)

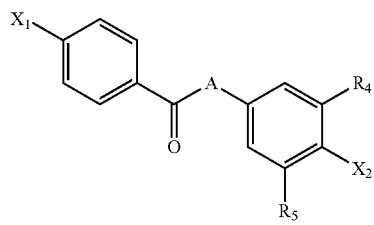

in which:
X1 is a halogen, a R1, or G1-R1 group;
A is a CH=CH or a CH2-CH2 group;
X2 is a G2-R2 group;
G1 and G2, identical or different, are an atom of oxygen or sulfur;
R1 is a hydrogen atom, an unsubstituted alkyl group, an aryl group or an alkyl group that is substituted by one or more halogen atoms, an alkoxy or an alkylthio group, cycloalkyl groups, cycloalkylthio groups or heterocyclic groups;
R2 is an alkyl group substituted by at least a —COOR3 group, wherein R3 is a hydrogen atom, or an alkyl group that is substituted or not by one or more halogen atoms, cycloalkyl groups, or heterocyclic groups;
R4 and R5, identical or different, corresponding to an alkyl group that is substituted or not by one or more halogen atoms, cycloalkyl groups, heterocyclic groups; or a pharmaceutically acceptable salt or a stereoisomer thereof.

2. The method of claim 1 wherein the compound is of general formula (I) in which:
X1 is a halogen, a R1, or G1-R1 group;
A is a CH=CH group;
X2 is a G2-R2 group;
G1 and G2, identical or different, are an atom of oxygen or sulfur;
R1 is an alkyl or cycloalkyl group having from one to seven carbon atoms, said alkyl or cycloalkyl group being substituted or not by one or more halogen atoms;
R2 is an alkyl group substituted by a —COOR3 group, wherein R3 represents a hydrogen atom or an alkyl group having from one to four carbon atoms;
R4 and R5 are an alkyl group having from one to four carbon atoms.

3. The method of claim 1 wherein the compound is of general formula (I) in which:
X1 is a R1 or G1-R1 group;
A is a CH2-CH2 group;
X2 is a G2-R2 group;
G1 is an atom of oxygen or sulfur and G2 represents an atom of oxygen;
R1 is an alkyl or cycloalkyl group having from one to seven carbon atoms;
R2 is an alkyl group substituted by at least a —COOR3 group, wherein R3 is a hydrogen atom or an alkyl group having from one to four carbon atoms;
R4 and R5 are an alkyl group having from one to four carbon atoms.

4. The method of claim 1 wherein the compound is of general formula (I) in which:
X1 is a halogen atom or a R1 or G1-R1 group;
A is a CH2-CH2 group;
X2 is a G2-R2 group;
G1 is an atom of oxygen or sulfur and G2 is an atom of oxygen;
R1 is an alkyl or cycloalkyl group that is substituted by one or more halogen atoms;
R2 is an alkyl group substituted or not by one or more halogen atoms and substituted by at least a —COOR3 group, wherein R3 is a hydrogen atom or an alkyl group having from one to four carbon atoms;
R4 and R5 are an alkyl group having from one to four carbon atoms.

5. The method of claim 1, wherein G2 is an oxygen atom and R2 is an alkyl group substituted by a —COOR3 group, wherein R3 is a hydrogen atom or an unsubstituted linear or branched alkyl group having from one to four carbon atoms.

6. The method of claim 1, wherein X1 is an alkylthio group that comprises an alkyl group that is linear or branched, having from one to seven carbon atoms that is substituted or not by one or more halogen atoms.

7. The method of claim 1, wherein said compound is selected in the group consisting of 1-[4-methylthiophenyl]-3-[3,5-dimethyl-4-carboxydimethylmethyloxy phenyl]prop-2-en-1-one, 1-[4-methylthiophenyl]-3-[3,5-dimethyl-4-isopropyloxy carbonyldimethylmethyloxyphenyl]prop-2-en-1-one, 1-[4-methylthiophenyl]-3-[3,5-dimethyl-4-tertbutyloxycarbonyldimethylmethyloxyphenyl] prop-2-en-1-one, 1-[4-trifluoromethylphenyl]-3-[3,5-dimethyl-4-tertbutyloxycarbonyl dimethylmethyloxyphenyl]prop-2-en-1-one, 1-[4-trifluoromethylphenyl]-3-[3,5-dimethyl-4-carboxydimethylmethyloxyphenyl]prop-2-en-1-one, 1-[4-trifluoromethyl oxyphenyl]-3-[3,5-dimethyl-4-tertbutyloxycarbonyldimethylmethyloxy phenyl] prop-2-en-1-one, 1-[4-trifluoromethyloxyphenyl]-3-[3,5-dimethyl-4-carboxydimethylmethyl oxyphenyl]prop-2-en-1-one, 2-[2,6-dimethyl-4-[3-[4-(methylthio)phenyl]-3-oxo-propyl] phenoxy]-2-methylpropanoic acid, and 2-[2,6-dimethyl-4-[3-[4-(methylthio) phenyl]-3-oxo-propyl]phenoxy]-2-methyl-propanoic acid isopropyl ester.

8. The method of claim 1, wherein the compound is orally administered.

9. The method of claim 1, wherein the compound is administered as an injectable suspension, a gel, an oil, a pill, a suppository, a powder, a gel cap, a capsule, an aerosol, a galenic form, a prolonged release formulation or a slow release form.

10. The method of claim 1, wherein the compound is administered in combination with metformin, insulin, a thiazolidinedione, a glitazone, or a statin.

11. The method of claim 1, comprising administering a pharmaceutical composition comprising a compound of General Formula (I) as defined in claim 1 or a pharmaceutically acceptable salt or a stereoisomer thereof.

12. The method of claim 11, wherein said composition is formulated in the form of injectable suspensions, a gel, an oil, a pill, a suppository, a powder, a gel cap, a capsule, an aerosol, a galenic form, a prolonged release formulation or a slow release form.

13. The method of claim 11, wherein said composition is in an oral form.

14. The method of claim 1, wherein said treatment delays progression of said liver disease.

15. The method of claim 11, wherein said treatment delays progression of said liver disease.

* * * * *